(12) United States Patent
Heffron et al.

(10) Patent No.: US 6,846,622 B1
(45) Date of Patent: Jan. 25, 2005

(54) TAGGED EPITOPE PROTEIN TRANSPOSABLE ELEMENT

(75) Inventors: Fred L. Heffron, West Linn, OR (US); David C. Parker, Portland, OR (US); Dolph D. Ellefson, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 09/979,338

(22) PCT Filed: May 26, 2000

(86) PCT No.: PCT/US00/14687
§ 371 (c)(1),
(2), (4) Date: Nov. 21, 2001

(87) PCT Pub. No.: WO00/71158
PCT Pub. Date: Nov. 30, 2000

Related U.S. Application Data
(60) Provisional application No. 60/136,210, filed on May 26, 1999.

(51) Int. Cl.[7] .............................. C12Q 1/68; C12Q 1/70; G01N 33/53
(52) U.S. Cl. ................................ 435/5; 435/6; 435/7.2; 435/7.31; 435/29; 435/320.1
(58) Field of Search ........................ 435/5, 6, 7.2, 7.31, 435/29, 320.1

(56) References Cited

PUBLICATIONS

Goldsby, RA et al. Kuby Immunology: 4th Edition. [2000] Goldsby et al, eds. W.H. Freeman and Co., New York. p. 209.*

McMahon et al., "Transposon–Mediated Random Insertions and Site–Directed Mutagenesis Prevent the Trafficking of a Mouse Mammary Tumor Virus Superantigen," *Virology* 243:354–365 (1998).

Szalay et al., "Presentation of Lysteria Monocytogenes Antigens by Major Histocompatibility Complex Class I Molecules to CD8 Cytotoxic T Lymphocytes Independent of Lysteriolysin Secretion and Virulence," *Eur. J. Immunol.* 24:1471–1477 (1994).

\* cited by examiner

*Primary Examiner*—Christina Chan
*Assistant Examiner*—F. Pierre Vandervegt
(74) *Attorney, Agent, or Firm*—Klarquist Sparkman, LLP

(57) ABSTRACT

A transposable element is provided that as a 3' and a 5' end. The transposable element includes a 5' recombining site 5' of a nucleic acid sequence encoding a selectable marker, a 3' recombining site 3' of the nucleic acid sequence encoding a selectable marker, a nucleic acid sequence encoding and MHC epitope 5' to the 5' recombining site or 3' to the 3' recombining site, and an insertion end comprising an inverted repeat sequence sufficient for integration of the transposable element at the 5' and the 3' end of the transposable element. In one embodiment, a transposable element is provided that has a 5' and a 3' end. The transposable element includes a 5' loxP sequence 5' of a nucleic acid encoding a selectable marker, a 3' loxP sequences 3' of a nucleic acid encoding the selectable marker, an MHC epitope 5' to the 5' loxP sequences or 3' of the 3' loxP sequence, an insertion end at the 5' end of the transposable element, and an insertion end at the 3' of the transposable element. A method is provided for detecting an antigenic epitope of a pathogen by infecting a pathogenic cell with a transposable element of the invention, wherein the infection results in the integration of the transposable element in a nucleic acid sequence of the bacterial cell; transforming the pathogenic cell with a vector comprising a transposase; contacting a eukaryotic cell that can internalize the pathogenic cell with the pathogenic cell infected with the transposable element; contacting the eukaryotic cell with a specific binding partner that recognizes the MHC epitope; identifying the labeled eukaryotic cells and externalizing the bacteria cell. The externalized bacterial cell may be grown to produce a population of bacterial cells, and the nucleic acid sequence of the bacterial cell that has the integrated transposable element is identified. This nucleic acid sequence encodes the antigenic element of the panthogen. A method is also provided for generating a carrier vaccine by infecting a bacterial cell with the transposable element of the invention, wherein the transposable further comprises an antigen associated with a disease operably linked to the MHC epitope of the transposable element. The infection of the bacteria results in the integration of the transposable element in a nucleic acid sequence of the bacterial cell. The pathogenic cell is then internalized into a eukaryotic cell and the eukaryotic cell is exposed to a specific bindned agent that recognizes the MHC epitope, identifying labeled eukaryotic cells are identified and lysed to externalized the bacteria cell, which is cultured to produce a population of bacterial cells. The nucleic acid sequence of the bacterial cell that has the integrated transposable element is identified, wherein the nucleic acid sequence encodes the antigenic element of the pathogen. The graving bacterial cell identified, and may be used as the carrier vaccine.

54 Claims, 13 Drawing Sheets

Figure 5: Construction of *Salmonella*-HIV epitope carrier vaccine strains. Tn5-HIV1/SOB (Human Immunodeficiency Virus 1/String of Beads) is transferred to a Nal$^r$ *Salmonella* recipient by conjugation. *Salmonella* transconjugants were pooled and phage P22 lysates were used Tn5 HIV1/SOB into *Salmonella typhimurium* (wild-type strain 14028s) and *Salmonella typhi* (Ty21a vaccine strain). Each phage recipient carries pBAD33cre, a plasmid that generates cre-recombinase upon induction with arabinose. Tn5-HIV1/SOB insertions are resolved of their kanamycin marker and Tn5-transposase by arabinose (1mM) induction of cre-recombinase. Tn5-HIV1/SOB carries a 6x-histidine site, the HLA-A2-restricted HTLV-1 *tax* epitope LLFGYPVYV and 5 HLA-A2 restricted HIV1 epitopes (p17 $_{77-85}$, p24 $_{193-203}$, RT $_{267-277}$, gp160 $_{313-322}$, and nef $_{71-80}$. Resolved in-frame insertions of Tn5-HIV1/SOB creates a 109 amino acid product encoding each epitope.

FIG. 6

92 amino acid resolved product encodes 3 tandem HLA-A2-restricted HER2/neu epitopes

Tn5 Mosaic End Sequences

DICE-I Resolved Sequence

```
          10        20        30        40        50
CTGTCTCTTATACACATCTCATATGGCTCTATCATCAACTTCGAAAAACT
GACAGAGAATATGTGTAGAGTATACCGAGATAGTAGTTGAAGCTTTTTGA
    L  S  L  I  H  I  S  Y  G  S  I  I  N  F  E  K  L 60        70        80        90       100
GGCGTTGACACCATCCATACTAGTAGATATCCACCACCACCACCACCACG
CCGCAACTGTGGTAGGTATGATCATCTATAGGTGGTGGTGGTGGTGGTGC
    A  L  T  P  S  I  L  V  D  I  H  H  H  H  H 110       120       130       140       150
GCCAGGACATAACTTCGTATAATGTATGCTATACGAAGTTATTTCTAGAA
CGGTCCTGTATTGAAGCATATTACATACGATATGCTTCAATAAAGATCTT
    G  Q  D  I  T  S  Y  N  V  C  Y  T  K  L  F  L  E 160       170
CCAGATGTGTATAAGAGACAG
GGTCTACACATATTCTCTGTC
    P  D  V  Y  K  R  Q
```

| Landmarks | Position |
|---|---|
| I-End | 1-19 |
| SIINFEKL | 28-52 |
| 5' PCR Site | 54-77 |
| 6-Histidine Site | 82 - 100 |
| LoxP | 109-143 |
| 3' PCR Site | 145-167 |
| O-End | 153-171 |

FIG. 12

DICE-II Resolved Sequence

```
         10         20         30         40         50
CTGTCTCTTATACACATCTCATATGGCCCGATGCGCAAAAACAACGCGTC
GACAGAGAATATGTGTAGAGTATACCGGGCTACGCGTTTTTGTTGCGCAG
   L  S  L  I  H  I  S  Y  G  P  M  R  K  N  N  A  S 60         70         80         90        100
CTTCGAAGCGCAGGGCGCGCTGGCGAACATCGCGGTGGACAAAGCGAACA
GAAGCTTCGCGTCCCGCGCGACCGCTTGTAGCGCCACCTGTTTCGCTTGT
 F  E  A  Q  G  A  L  A  N  I  A  V  D  K  A  N 110        120        130        140        150
ACAAACGCGATATCCACCACCACCACCACGGCCAGGACATAACTTCG
TGTTTGCGCTATAGGTGGTGGTGGTGGTGCCGGTCCTGTATTGAAGC
 N  K  R  D  I  H  H  H  H  H  G  Q  D  I  T  S 160        170        180        190        200
TATAATGTATGCTATACGAAGTTATTTCTAGAACCAGATGTGTATAAGAG
ATATTACATACGATATGCTTCAATAAAGATCTTGGTCTACACATATTCTC
 Y  N  V  C  Y  T  K  L  F  L  E  P  D  V  Y  K  R

ACAG
TGTC
 Q
```

| Landmarks | Position |
|---|---|
| I-End | 1-19 |
| 5' PCR Site | 25-45 |
| 5' Asparyginyl Endopeptidase Cleavage Site | 34-45 |
| ASFEAQGALANIAVDKA | 46-84 |
| 5' Asparyginyl Endopeptidase Cleavage Site | 97-108 |
| 6-Histidine Site | 115-132 |
| LoxP | 142-175 |
| 3' PCR Site | 178-198 |
| O-End | 186-204 |

FIG. 13

SEQUENCE LISTING

```
<160> NUMBER OF SEQ ID NOS: 33

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Primer that
      can be used to sequence the gene in which a
      transposable element inserted.

<400> SEQUENCE: 1
gcggatatcc accaccacca cc                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Primer that
      can be used to sequence the gene in which a
      transposable element inserted.

<400> SEQUENCE: 2
tatgcccggg ccgtggtggt gg                                              22

<210> SEQ ID NO 3
<211> LENGTH: 18
<212> TYPE: DNA
<213> ORGANISM: Escherichia coli

<400> SEQUENCE: 3
gatgtgtata agagacag                                                   18

<210> SEQ ID NO 4
<211> LENGTH: 19
<212> TYPE: DNA
<213> ORGANISM: Escherichia coli

<400> SEQUENCE: 4
ctgactctta tacacaagt                                                  19

<210> SEQ ID NO 5
<211> LENGTH: 19
<212> TYPE: DNA
<213> ORGANISM: Escherichia coli

<400> SEQUENCE: 5
ctgtctctta tacacatct                                                  19

<210> SEQ ID NO 6
<211> LENGTH: 8
```

```
<212> TYPE: PRT
<213> ORGANISM: Artificial Sequence
<220> FEATURE:
<223> OTHER INFORMATION: Description of Artificial Sequence: Ovalbumin
      epitope

<400> SEQUENCE: 6

Ser Ile Ile Asn Phe Glu Lys Leu
  1               5

<210> SEQ ID NO 7
<211> LENGTH: 9
<212> TYPE: PRT
<213> ORGANISM: Human T-cell lymphotropic virus type 1

<400> SEQUENCE: 7

Leu Leu Phe Gly Tyr Pro Val Tyr Val
  1               5

<210> SEQ ID NO 8
<211> LENGTH: 19
<212> TYPE: DNA
<213> ORGANISM: Escherichia coli

<400> SEQUENCE: 8
ctgactctta tacacaagt                                               19

<210> SEQ ID NO 9
<211> LENGTH: 19
<212> TYPE: DNA
<213> ORGANISM: Escherichia coli

<400> SEQUENCE: 9
ctgtctctta tacacatct                                               19

<210> SEQ ID NO 10
<211> LENGTH: 19
<212> TYPE: DNA
<213> ORGANISM: Escherichia coli

<400> SEQUENCE: 10
ctgtctcttg atcagatct                                               19

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: A 5' PCR
      site

<400> SEQUENCE: 11
gttgacacca tccatactag taga                                         24

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Sequence of
      6X histidine
<220> FEATURE:
<221> NAME/KEY: CDS
<222> LOCATION: (1)..(18)

<400> SEQUENCE: 12
```

```
cac cac cac cac cac cac g                                          19
His His His His His His
  1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Sequence of
      6X histidine

<400> SEQUENCE: 13

His His His His His His
  1               5

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: LoxP
      sequence

<400> SEQUENCE: 14
ataacttcgt ataatgtatg ctatacgaag ttatt                             35

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: 3' PCR site

<400> SEQUENCE: 15
ctagaaccag atgtgtataa gaga                                         24

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: 5' PCR site

<400> SEQUENCE: 16
ggcccgatgc gcaaaaacaa c                                            21

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: 5'
      Asparyginyl Endopeptidase cleavage site

<400> SEQUENCE: 17
cgcaaaaaca ac                                                      12

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence: 3'
      Asparyginyl endopeptidase cleavage site

<400> SEQUENCE: 18
```

```
aacaacaaac gc                                                              12

<210> SEQ ID NO 19
<211> LENGTH: 51
<212> TYPE: DNA
<213> ORGANISM: Artificial Sequence
<220> FEATURE:
<221> NAME/KEY: CDS
<222> LOCATION: (1)..(51)
<220> FEATURE:
<223> OTHER INFORMATION: Description of Artificial Sequence: The I-Ab
      restricted T-cell epitope region of DICE II

<400> SEQUENCE: 19 gcg tcc ttc gaa gcg cag ggc gcg ctg gcg aac atc gcg gtg gac aaa        48
Ala Ser Phe Glu Ala Gln Gly Ala Leu Ala Asn Ile Ala Val Asp Lys
 1               5                  10                  15 gcg                                                                    51
Ala

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: The I-Ab
      restricted T-cell epitope region of DICE II

<400> SEQUENCE: 20

Ala Ser Phe Glu Ala Gln Gly Ala Leu Ala Asn Ile Ala Val Asp Lys
 1               5                  10                  15

Ala

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: 3' PCR site

<400> SEQUENCE: 21
ctagaaccag atgtgtataa g                                                21

<210> SEQ ID NO 22
<211> LENGTH: 171
<212> TYPE: DNA
<213> ORGANISM: Artificial Sequence
<220> FEATURE:
<223> OTHER INFORMATION: Description of Artificial Sequence: DICE I
      sequence
<220> FEATURE:
<221> NAME/KEY: CDS
<222> LOCATION: (1)..(171)

<400> SEQUENCE: 22 ctg tct ctt ata cac atc tca tat ggc tct atc atc aac ttc gaa aaa        48
Leu Ser Leu Ile His Ile Ser Tyr Gly Ser Ile Ile Asn Phe Glu Lys
 1               5                  10                  15 ctg gcg ttg aca cca tcc ata cta gta gat atc cac cac cac cac cac        96
Leu Ala Leu Thr Pro Ser Ile Leu Val Asp Ile His His His His His
                20                  25                  30 cac ggc cag gac ata act tcg tat aat gta tgc tat acg aag tta ttt       144
His Gly Gln Asp Ile Thr Ser Tyr Asn Val Cys Tyr Thr Lys Leu Phe
                35                  40                  45 cta gaa cca gat gtg tat aag aga cag                                   171
Leu Glu Pro Asp Val Tyr Lys Arg Gln
```

```
                50                  55

<210> SEQ ID NO 23
<211> LENGTH: 57
<212> TYPE: PRT
<213> ORGANISM: Artificial Sequence
<220> FEATURE:
<223> OTHER INFORMATION: Description of Artificial Sequence: DICE I
      sequence

<400> SEQUENCE: 23

Leu Ser Leu Ile His Ile Ser Tyr Gly Ser Ile Ile Asn Phe Glu Lys
  1               5                  10                  15

Leu Ala Leu Thr Pro Ser Ile Leu Val Asp Ile His His His His
             20                  25                  30

His Gly Gln Asp Ile Thr Ser Tyr Asn Val Cys Tyr Thr Lys Leu Phe
         35                  40                  45

Leu Glu Pro Asp Val Tyr Lys Arg Gln
         50                  55

<210> SEQ ID NO 24
<211> LENGTH: 204
<212> TYPE: DNA
<213> ORGANISM: Artificial Sequence
<220> FEATURE:
<223> OTHER INFORMATION: Description of Artificial Sequence: DICE II
      Sequence
<220> FEATURE:
<221> NAME/KEY: CDS
<222> LOCATION: (1)..(204)

<400> SEQUENCE: 24 ctg tct ctt ata cac atc tca tat ggc ccg atg cgc aaa aac aac gcg      48
Leu Ser Leu Ile His Ile Ser Tyr Gly Pro Met Arg Lys Asn Asn Ala
  1               5                  10                  15 tcc ttc gaa gcg cag ggc gcg ctg gcg aac atc gcg gtg gac aaa gcg      96
Ser Phe Glu Ala Gln Gly Ala Leu Ala Asn Ile Ala Val Asp Lys Ala
             20                  25                  30 aac aac aaa cgc gat atc cac cac cac cac cac ggc cag gac ata         144
Asn Asn Lys Arg Asp Ile His His His His His Gly Gln Asp Ile
         35                  40                  45 act tcg tat aat gta tgc tat acg aag tta ttt cta gaa cca gat gtg     192
Thr Ser Tyr Asn Val Cys Tyr Thr Lys Leu Phe Leu Glu Pro Asp Val
     50                  55                  60 tat aag aga cag                                                     204
Tyr Lys Arg Gln
 65

<210> SEQ ID NO 25
<211> LENGTH: 68
<212> TYPE: PRT
<213> ORGANISM: Artificial Sequence
<220> FEATURE:
<223> OTHER INFORMATION: Description of Artificial Sequence: DICE II
      Sequence

<400> SEQUENCE: 25

Leu Ser Leu Ile His Ile Ser Tyr Gly Pro Met Arg Lys Asn Asn Ala
  1               5                  10                  15

Ser Phe Glu Ala Gln Gly Ala Leu Ala Asn Ile Ala Val Asp Lys Ala
             20                  25                  30

Asn Asn Lys Arg Asp Ile His His His His His Gly Gln Asp Ile
         35                  40                  45
```

```
Thr Ser Tyr Asn Val Cys Tyr Thr Lys Leu Phe Leu Glu Pro Asp Val
    50                  55                  60

Tyr Lys Arg Gln
 65
```

<210> SEQ ID NO 26
<211> LENGTH: 49
<212> TYPE: PRT
<213> ORGANISM: Artificial Sequence
<220> FEATURE:
<223> OTHER INFORMATION: Description of Artificial Sequence: Amino acid
      resolved procut using the construct shown in FIG
      2.

<400> SEQUENCE: 26

```
Leu Ser Leu Asp Gln Ile Ser Tyr Gly Pro Gly Ser Ile Ile Asn Phe
 1               5                  10                  15

Glu Lys Leu Ala Asp Ile His His His His His Gly Pro Gly Ile
            20                  25                  30

Thr Ser Tyr Ser Leu Glu Tyr Thr Lys Gly Arg Ser Ser Pro Gly Gly
        35                  40                  45

Ser
```

<210> SEQ ID NO 27
<211> LENGTH: 82
<212> TYPE: PRT
<213> ORGANISM: Artificial Sequence
<220> FEATURE:
<223> OTHER INFORMATION: Description of Artificial Sequence: Amino acid
      resolved product using the construct shown in FIG
      5.

<400> SEQUENCE: 27

```
Leu Ser Leu Asp Gln Ile Ser Tyr Gly Pro Met Leu Leu Phe Gly Tyr
 1               5                  10                  15

Pro Val Tyr Val Ala His His His His His Met Lys Ile Phe Gly
            20                  25                  30

Ser Leu Ala Phe Leu Ala Met Val Met Ala Gly Val Gly Ser Pro Tyr
        35                  40                  45

Val Ala Met Ile Ile Ser Ala Val Val Gly Ile Leu Ala Gly Pro Gly
    50                  55                  60

Ile Thr Ser Tyr Ser Leu Glu Tyr Thr Lys Gly Arg Ser Ser Pro Gly
 65                  70                  75                  80

Gly Ser
```

<210> SEQ ID NO 28
<211> LENGTH: 109
<212> TYPE: PRT
<213> ORGANISM: Artificial Sequence
<220> FEATURE:
<223> OTHER INFORMATION: Description of Artificial Sequence: Amino Acid
      resolved product using the construct shown in FIG
      6.

<400> SEQUENCE: 28

```
Leu Ser Leu Asp Gln Ile Ser Tyr Gly Pro Met Leu Leu Phe Gly Tyr
 1               5                  10                  15

Pro Val Tyr Val Ala His His His His His Met Ser Leu Tyr Asn
            20                  25                  30

Thr Val Ala Thr Leu Ala Met Gly His Gln Ala Ala Met Gln Met Leu
        35                  40                  45
```

-continued

```
Lys Glu Ala Met Val Leu Asp Val Gly Asp Ala Tyr Phe Ser Val Ala
         50                  55                  60
Met Arg Gly Pro Gly Arg Ala Phe Val Thr Ile Ala Met Gln Val Pro
 65                  70                  75                  80
Leu Arg Pro Met Thr Tyr Lys Ala Gly Pro Gly Ile Thr Ser Tyr Ser
                 85                  90                  95
Leu Glu Tyr Thr Lys Gly Arg Ser Ser Pro Gly Gly Ser
            100                 105

<210> SEQ ID NO 29
<211> LENGTH: 57
<212> TYPE: PRT
<213> ORGANISM: Artificial Sequence
<220> FEATURE:
<223> OTHER INFORMATION: Description of Artificial Sequence: Amino acid
      resolved product using the construct shown in FIG
      7.

<400> SEQUENCE: 29

Leu Ser Leu Ile His Ile Ser Tyr Gly Ser Ile Ile Asn Phe Glu Lys
  1               5                  10                  15
Leu Ala Leu Thr Pro Ser Ile Leu Val Asp Ile His His His His
             20                  25                  30
His Gly Gln Asp Ile Thr Ser Tyr Asn Val Cys Tyr Thr Lys Leu Phe
         35                  40                  45
Leu Glu Leu Asp Val Tyr Lys Arg Gln
     50                  55

<210> SEQ ID NO 30
<211> LENGTH: 73
<212> TYPE: PRT
<213> ORGANISM: Artificial Sequence
<220> FEATURE:
<223> OTHER INFORMATION: Description of Artificial Sequence: Amino acid
      resolved product using the construct shown in FIG
      8.

<400> SEQUENCE: 30

Leu Ser Leu Ile His Ile Ser Tyr Gly Arg Lys Asn Asn Ala Ser Phe
  1               5                  10                  15
Glu Ala Gln Gly Ala Leu Ala Asn Ile Ala Val Asp Lys Ala Asn Asn
             20                  25                  30
Lys Arg Leu Thr Pro Ser Ile Leu Val Asp Ile His His His His
         35                  40                  45
His Gly Gln Asp Ile Thr Ser Tyr Asn Val Cys Tyr Thr Lys Leu Phe
     50                  55                  60
Leu Glu Leu Asp Val Tyr Lys Arg Gln
 65                  70

<210> SEQ ID NO 31
<211> LENGTH: 92
<212> TYPE: PRT
<213> ORGANISM: Artificial Sequence
<220> FEATURE:
<223> OTHER INFORMATION: Description of Artificial Sequence: Amino acid
      resolved product using the construct shown in f
      FIG 9.

<400> SEQUENCE: 31

Leu Ser Leu Ile His Ile Ser Tyr Gly Leu Leu Phe Gly Tyr Pro Val
  1               5                  10                  15
Tyr Val Ala Leu Thr Pro Ser Ile Leu Val Asp Ile His His His His
```

-continued

```
                    20                  25                  30
His His Met Lys Ile Phe Gly Ser Leu Ala Phe Leu Ala Met Val Met
            35                  40                  45

Ala Gly Val Gly Ser Pro Tyr Val Ala Met Ile Ile Ser Ala Val Val
    50                  55                  60

Gly Ile Leu Ala Gly Gln Asp Ile Thr Ser Tyr Asn Val Cys Tyr Thr
65                  70                  75                  80

Lys Leu Phe Leu Glu Leu Asp Val Tyr Lys Arg Gln
                85                  90
```

<210> SEQ ID NO 32
<211> LENGTH: 119
<212> TYPE: PRT
<213> ORGANISM: Artificial Sequence
<220> FEATURE:
<223> OTHER INFORMATION: Description of Artificial Sequence: Amino acid resolved product using the construct shown in FIG 10.

<400> SEQUENCE: 32

```
Leu Ser Leu Ile His Ile Ser Tyr Gly Leu Leu Phe Gly Tyr Pro Val
1               5                   10                  15

Tyr Val Ala Leu Thr Pro Ser Ile Leu Val Asp Ile His His His
                20                  25                  30

His His Met Ser Leu Tyr Asn Thr Val Ala Thr Leu Ala Met Gly His
            35                  40                  45

Gln Ala Ala Met Gln Met Leu Lys Glu Ala Met Val Leu Asp Val Gly
    50                  55                  60

Asp Ala Tyr Phe Ser Val Ala Met Arg Gly Pro Gly Arg Ala Phe Val
65                  70                  75                  80

Thr Ile Ala Met Gln Val Pro Leu Arg Pro Met Thr Tyr Lys Ala Gly
                85                  90                  95

Gln Asp Ile Thr Ser Tyr Asn Val Cys Tyr Thr Lys Leu Phe Leu Glu
                100                 105                 110

Leu Asp Val Tyr Lys Arg Gln
        115
```

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 33
ctactagtat ggatggtgtc                                              20

TAGGED EPITOPE PROTEIN TRANSPOSABLE ELEMENT

This is a § 371 U.S. national stage of PCT/US00/14687 filed May 26, 2000, which was published in English under PCT Article 21(2), which claims the benefit of U.S. provisional application No. 60/136,210 filed May 26, 1999.

FIELD

This invention relates to transposons, specifically to the use of transposons to insert into a genome to identify antigenic epitopes. This invention also relates to the identification of vaccine antigens.

BACKGROUND

The immune system is alerted to the presence of foreign infectious agents by the presentation of complexes on the surface of the infected cell. The complexes are composed of antigens derived from the pathogen and proteins of the Major Histocompatability Complex (MHC). Two separate pathways, MHC I and MHC II, drive cellular and humoral immune responses, respectively. In general, MHC I-presented antigens are derived from cytoplasmic proteins. However in antigen presenting cells (APC), the MHC I-presented antigens are derived from an alternate pathway through a lysosomal compartment (Morrison et al. *J. Exp. Med* 163:903–21, 1986; Pfeifer et al. *Nature* 361:359–62, 1993.) MHC II antigens are generally derived from pinocytotic or phagocytic mechanisms (Morrison et al. *J. Exp. Med* 163:903–21, 1986).

Of the many pathogenic bacteria capable of mediating disease in humans and animals, intracellular pathogens present unique challenges in attempting to understand bacteria/host cell interactions. Intracellular pathogens are divided into two groups: those that reside within a phagolysosomal compartment (*Salmonella* sp, *Mycobacterium tuberculosis*, etc.) and those which reside within the cytoplasm (*Listeria monocytogenes*, *Shigella* sp, etc.). Intracellular pathogens adapt to their host cell environment by the selective secretion of proteins designed to alter the normal structural and metabolic machinery of the host cell, thus promoting bacterial survival and avoidance of host immune surveillance. Both phagolysosomal and cytoplasmic intracellular pathogens secrete proteins known to mediate their effects specifically within the host cell cytoplasm (Cornelis and Wolf-Watz, *Mol. Microbiol.* 23:861–7, 1997; Collazo and Galan, *Mol. Microbiol.* 24:747–56, 1997; Fu and Galan, *Mol. Microbiol.* 27:359–68, 1998). Because cytoplasmic localization of the bacterial protein also infers access to the degradative machinery of the host cell proteosome, these proteins were named Class I Accessible Proteins (CAPs).

Vaccination with *Salmonella* results in the production of a strong cellular and humoral response against the bacteria itself (Sztein et al., *J Immunol* 155:3987–93, 1995). However, the heterologous-antigen specific immune response is variable and depends on several factors, including the nature of the antigen itself, the type of cell and tissue in which the antigen is expressed, the level of expressi n, and whether the antigen is presented and processed by the class I or class II MHC pathways. Results using either the SIV capsid antigen or the malaria circumspor zoite antigen, demonstrate that antigen-specific cytotoxic T lymphocyte (CTL) responses are induced when the antigen is expressed in *Salmonella* (Flynn et al., *Mol. Microbiol.* 4:2111–8, 1990; Sadoff et al., *Science*, 240:336–8, 1988; Valentine et al., *Vaccine.* 14:138–46, 1996). Other antigens have failed to elicit a CTL response even in similar expression systems (Tite et al., *Immunology* 70(4):540–6 1990).

A plasmid containing a gene for a foreign antigen expressed from a eukaryotic promoter resulted in a strong cell-mediated response against the foreign antigen (Darji et al., *Cell* 91(6):765–75 1997); Schodel and Curtiss, *Dev. Biol Stand* 84:245–53, 1995).

A significant advance in the area of cancer vaccination has been the identification of tumor-specific epitopes. In general, cancer vaccines attempt to elicit an immune response to tumors by directing tumor-specific epitopes to various compartments of the immune system. Several strategies, which include vaccines composed of DNA, proteins, peptides, whole cells, carbohydrates and recombinant vectors, have been used to generate tumor vaccines. The use of recombinant vectors includes the use of live carrier vectors such as vaccinia, BCG, canarypox, and *Salmonella*, which are designed to stimulate the appropriate immune responses to tumors and infectious agents as a by-product of infection. Effective vaccines need to elicit strong, long-term, and multi-haplotype protection against a tenacious cancer. An ideal vaccine would satisfy these requirements and elicit an inescapable immune response by delivering a wide-variety of antigens.

SUMMARY

A transposable element is provided that has a 3' and a 5' end. The transposable element includes a 5' recombining site 5' of a nucleic acid sequence encoding a selectable marker, a 3' recombining site 3' of the nucleic acid sequence encoding a selectable marker, a nucleic acid sequence encoding an MHC epitope 5' to the 5' recombining site or 3' to the 3' recombining site, and an insertion end comprising an inverted repeat sequence sufficient for integration of the transposable element at the 5' and the 3' end of the transposable element.

In one embodiment, a transposable element is provided that has a 5' and a 3' end. The transposable element includes a 5' loxP sequence 5' of a nucleic acid encoding a selectable marker, a 3' loxP sequence 3' of a nucleic acid encoding the selectable marker, an MHC epitope 5' to the 5' loxP sequences or 3' of the 3' loxP sequence, an insertion end at the 5' end of the transposable element, and an insertion end at the 3' of the transposable element In another embodiment, a transposable element is provided that has a 5' and a 3' end. The transposable element includes an antibiotic resistance cassette, a 5' loxP sequence 5' of the antibiotic resistance cassette and a 3' loxP sequence 3' of the antibiotic resistance cassette, an MHC epitope 5' to the 5' loxP sequence or 3' of the 3' loxP sequence, an affinity tag, an insertion end at the 5' end of the transposable element; and an insertion end at the 3' of the transposable element.

In yet another embodiment a transposable element is provided that has a 5' and a 3' end. The transposable element includes a kanamycin antibiotic resistance cassette, a loxP sequence comprising the sequence shown in SEQ ID NO 11 located 5' and 3' to the antibiotic resistance cassette, a nucleic acid sequence encoding a transposase, a nucleic acid sequence encoding a MHC epitope, a nucleic acid sequence encoding a 6× histidine affinity tag, an insertion end at the 5' end of the transposable element; and an insertion end at the 3' of the transposable element.

Transposable elements have been engineered which can introduce in-frame insertions throughout the chromosome of a bacterium. This system "tags" the gene and resulting protein, for use in identifying proteins secreted across the membranes of the cell infected by the bacterium.

One particular embodiment of the method includes infecting a pathogenic cell with a transposable element of the invention, wherein the infection results in the integration of the transposable element in a nucleic acid sequence of the bacterial cell, transforming the pathogenic cell with a vector comprising a transposase, contacting a eukaryotic cell that can internalize the pathogenic cell with the pathogenic cell infected with the transposable element, contacting the eukaryotic cell with a labeled antibody that recognizes the MHC epitope, identifying the labeled eukaryotic cells, lysing the labeled eukaryotic cells to externalize the bacteria cell, growing the externalized bacterial cell to produce a population of bacterial cells; and identifying the nucleic acid sequence of the bacterial cell that has the integrated transposable element, wherein this nucleic acid sequence encodes the antigenic element of the pathogen.

In another embodiment, a method is provided for generating a carrier vaccine. The method includes infecting a bacterial cell with the transposable element of the invention, wherein the transposable element further comprises an antigen associated with a disease operably linked to the MHC epitope of the transposable element, wherein the infection of the bacteria results in the integration of the transposable element in a nucleic acid sequence of the bacterial cell. The method also includes contacting a eukaryotic cell that can internalize the pathogenic cell with the pathogenic cell infected with the transposable element, contacting the eukaryotic cell with a labeled antibody that recognizes the MHC epitope, identifying the labeled eukaryotic cells, lysing the labeled eukaryotic cells to externalize the bacteria cell, growing the externalized bacterial cell to produce a population of bacterial cells; identifying the nucleic acid sequence of the bacterial cell that has the integrated transposable element, wherein the nucleic acid sequence encodes the antigenic element of the pathogen; and growing the identified bacterial cell identified. The identified bacterial cell is the carrier vaccine.

BRIEF DESCRIPTION OF THE FIGURES

FIG. 6 is a schematic representation showing the Tn5-HIV1/SOB construct.

FIG. 11 shows the Tn5 Mosaic end sequences.

FIG. 12 shows the DICE-I Resolved Sequence.

FIG. 13 shows the DICE-II Resolved Sequence.

SEQUENCE LISTING

Figure 1:
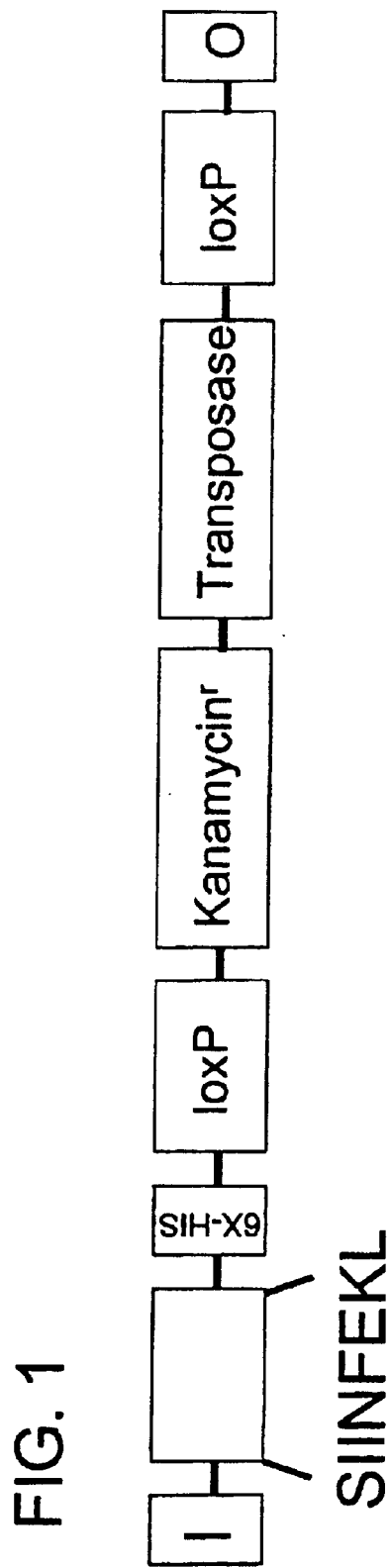
FIG. 1 is a schematic representation of the Tn5-DICE transposon.

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NO 1 is the nucleic acid sequence of a primer that can be used to sequence the gene in which a transposable element inserted.

SEQ ID NO 2 is the nucleic acid sequence of a primer that can be used to sequence the gene in which a transposable element inserted.

SEQ ID NO 3 is the sequence of the O end.

SEQ ID NO 4 is the sequence of a mosaic end.

SEQ ID NO 5 is the sequence of an 1 end.

SEQ ID NO 6 is the SIINFEKL epitope.

SEQ ID NO 7 is the LLFGYPVYV epitope.

SEQ ID NO 8 is the ASFEAQGALANIAVDKA epitope.

SEQ ID NO 9 is the sequence of a 5' PCR site, shown as position 54–77 of FIG. 12.

SEQ ID NO 10 is the sequence of the 6× histidine, shown as position 82–100 of FIG. 12.

SEQ ID NO 11 is the sequence of the loxP, shown a position 109–143 of FIG. 12.

SEQ ID NO 12 is the sequence of the 3' PCR site, shown as position 145–167 of FIG. 12.

SEQ ID NO 13 is the sequence of a 5' PCR site, shown as position 25–45 of FIG. 13.

SEQ ID NO 14 is the sequence of the 5' asparyginyl endopeptidase cleavage site, shown as position 34–45 of FIG. 13.

SEQ ID NO 15 is the sequence of the 3' asparyginyl endopeptidase cleavage site, shown as position 97–108 of FIG. 13.

DETAILED DESCRIPTION OF SEVERAL EMBODIMENTS

Transposable elements have been engineered which can introduce in-frame insertions throughout the chromosome of a bacterium. This system "tags" the gene and resulting protein, allowing the identification of proteins secreted across the membranes of the cell infected by the bacterium. In one embodiment, the transposable elements contain an antibiotic resistance cassette, two minimal loxP recombination sites, an MHC class I or class II epitope, and flanking insertion ends. A transposase, such as the cre recombinase protein is expressed in trans from a plasmid, or can be included in the transposable element. The cre recombinase loops out the intervening sequences containing the antibiotic resistance cassette. When the transposable elements insert within a gene, the resolved insertion places the MHC class I or class II epitope in frame with the gene. Restriction sites allow the introduction of other marker proteins.

Certain embodiments of this technology, termed Disseminated Insertions of Class-I Epitopes (DICE-I) (DICE-II for class II epitopes), allow the rapid and accurate identification of proteins involved in bacterial pathogenesis. Uses for this technology include the identification of vaccine and drug targets for therapy of a variety of bacteria pathogenic to humans and animals. In addition, this system can facilitate the assignment of function to genes previously identified through genomic analysis. This method is also directly applicable to the generation of haplotype independent cytotoxic T lymphocyte (CTL) response to a given antigen as a way of assessing patient immune response; measuring CTL response as a way of diagnosing specific infections; development of human and animal vaccines that require a strong CTL response; identification of new bacterial carrier proteins that can be used to generate a CTL response to infection; and augmentation of the immune response by delivery of eukaryotic immune effectors.

The identification of CAPs secreted by the MHC class I or class II pathway in response to host cell interactions are invaluable in the design of better bacterial carrier vaccines and to identify entire new classes of potentially useful vaccine target proteins from different pathogens and tumors, since CAPs possess unique access to the host's antigen processing and presentation machinery. In addition, because a substantial proportion of open reading frames derived from whole genome analysis have no known function, a system which allows the identification of CAPs secreted in response to host cell interactions, is an invaluable tool for understanding many levels of pathogen/host cell interactions. Furthermore, CAPs represent useful vehicles for the delivery of foreign epitopes by bacterial vaccine strains, such as *Salmonella*.

DICE-I and DICE-II have several inherent strengths in the identification of CAPs. In some embodiments, DICE selection is conditional, host class I-accessible proteins are isolated as a consequence of being processed and presented in the context of H-2 $K^b$, and host class I-accessible proteins are isolated as a consequence of being processed and presented in the context of I-$A^b$. Moreover, only in-frame insertions, which do not alter secretory signals, are recovered. Selection can be made simple and powerful, with interesting strains quickly recovered from a large population of infected cells by flow cytometry. Since selection is specific, bacteria cannot be recovered from macrophages that have presented a MHC epitope from non-secreted intracellular proteins derived by bacterial attrition within the phago-lysosome because these bacteria would not be viable. Moreover, because the transposable elements can carry an affinity tag such as 6x-hisitdine, the subcellular location of the protein can be visualized by microscopy, thereby enabling functional and phenotypic inferences to be drawn about proteins with no known homology. Also, the protein can be readily assessed as an epitope carrier by attenuating the strain and immunizing the appropriate animal model.

Abbreviations and Definitions

The following definitions and methods are provided to better define the present invention and to guide those of ordinary skill in the art in the practice of the present invention. As used herein and in the appended claims, the singular forms "a" or "an" or "the" include plural referents unless the context clearly indicates otherwise. Thus, for example, reference to "transposon" includes a plurality of such transposons and reference to "the antigen" includes reference to one or more antigens and equivalents thereof known to those skilled in the art, and so forth.

Unless defined otherwise, all technical and scientific terms used herein have the same meaning as commonly understood to one of ordinary skill in the art to which this invention belongs.

MOI multiplicity of infection

RT room temperature

Affinity Tag: A sequence which can be included in a transposable element which can aid in the purification of the protein in which the transposable element inserts. The term affinity tag refers to the nucleic acid sequence for the tag, and the tag protein sequence encoded by the nucleic acid sequence. Examples of affinity tags include, but are not limited to: histidine, such as 6xhistidine, S-tag, glutathione-S-transferase (GST) and streptavidin.

Animal: Living multicellular vertebrate organisms, a category which includes, for example, mammals, primates, and birds.

Antibiotic resistance cassette: A selectable marker that is a nucleic acid sequence which confers resistance to that antibiotic in a host cell in which the nucleic acid is translated. Examples of antibiotic resistance cassettes include, but are not limited to kanamycin, ampicillin, tetracycline, chloramphenicol, neomycin, hygromycin, zeocin.

Cancer: Malignant neoplasm that has undergone characteristic anaplasia with loss of differentiation, increased rate of growth, invasion of surrounding tissue, and is capable of metastasis.

CAPs: MHC Class I or Class II accessible proteins.

cDNA (complementary DNA): A piece of DNA lacking internal, non-coding segments (introns) and regulatory sequences which determine transcription. cDNA may be synthesized in the laboratory by reverse transcription from messenger RNA extracted from cells.

Deletion: The removal of a sequence of DNA, the regions on either side being joined together.

DNA: Deoxyribonucleic acid. DNA is a long chain polymer which comprises the genetic material of most living organisms (some viruses have genes comprising ribonucleic acid, RNA). The repeating units in DNA polymers are four different nucleotides, each of which comprises one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Insertion Ends: Nucleic acid sequences that bind transposase. In general, insertion ends are 19 base pairs in length. In the constructs described herein they are located 5' (the 5' insertion end) to the MHC epitope and 3' (the 3' insertion end) to the 3' loxP sequence. Examples of 5' insertion ends include, but are not limited to, the I end of IS50R (e.g. SEQ ID NO:5, Genbank Accession No. U3299 1.1) and the mosaic sequence (SEQ ID NO:4, see Goryshin and Reznikoff *Journal of Biological Chemistry* 273(13):7367–74). Examples of 3' insertion ends include, but are not limited to, the O end of IS50R (e.g. SEQ ID NO:3, Genbank accession No. U00004.1 and the mosaic sequence shown herein (see FIG. 11).

IS50R: Insertion sequence (IS) type 50R. This IS element ends in short inverted terminal repeats, designated the I and O ends (insertion ends) (e.g. see Genbank Accession Nos. U32991.1 and U00004.1, respectively).

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

loxP sequence: A target sequence recognized by the bacterial cre recombinase; loxP is the recombination site for the enzyme Cre recombinase. The loxP sequence was originally derived from bacteriophage Pl (see Hoekstra et. Al., *Proceedings of the National Academy of Sciences* 88(12): 5457–61 1991). In one embodiment, loxP sites are defined by the sequence ATAACTTCGTATAATGTATGCTA TACGAAGTTAT. A "minimal" loxP sequence is the minimal sequence recognized by the cre recombinase. In one embodiment, minimal loxP sequence is as described in Hoekstra et. Al., *Proceedings of the National Academy of Sciences* 88(12):5457–61 1991. Specific, non-limiting examples include, but are not limited to, the sequence listed as Genbank accession No. MI0494.1. The 5' and 3' loxP sequences must be identical. The loxP sites are represented by the sequence defined above to prevent premature transcriptional termination.

As used herein, these sequences are located upstream and downstream (5' and 3', respectively) to a sequence encoding a selectable marker.

Mammal: This term includes both human and non-human mammals. Similarly, the terms "subject," "patient," and "individual" include human and veterinary subjects.

MHC Epitopes: Epitopes presented through the class I or class II MHC pathway, for which at least one antibody is available. The antibody binds preferentially to the epitope complexed with MHC molecules, not to the free epitope. Examples of class I MHC epitopes include, but are not limited to the ovalbumin epitope, SIINFEKL (SEQ ID NO 6), and the HLA-A2 restricted human T-cell epitope LLFGYPVYV (SEQ ID NO 7) from HTLV-1 (see Genbank Accession No. B45714). Examples of class I MHC epitopes include, but are not limited to, the I-A$^b$ restricted T-cell epitope, ASFEAQGALANIAVDKA (SEQ ID NO 8).

A MHC epitope "adjoins" a recombining site (i.e., a 5' or 3' recombining site) when the nucleic acid sequence encoding the MHC epitope is located either 5' of the 5' recombining site of 3' of the 3' recombining site in a transposable element. Upon recombination of a transposable element with a genome, insertion a of the MHC epitope in the genome occurs, and the MHC epitope is expressed along with a cellular protein. In one embodiment, the MHC epitope is located within about 5000 bp of the recombining site. Alternatively, the MHC epitope can be located within about 1000 bp., 500 bp, 100 bp, 20 bp, 10 bp, or 0 by from the recombining site.

Oligonucleotide: A linear polynucleotide sequence of up to about 200 nucleotide bases in length, for example a polynucleotide (such as DNA or RNA) which is at least 6 nucleotides, for example at least 15, 50, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame): A series of nucleotide triplets (codons) coding for amino acids without any termination codons. These sequences are usually translatable into a peptide.

Ortholog: Two nucleotide sequences are orthologs of each other if they share a common ancestral sequence, and diverged when a species carrying that ancestral sequence split into two species. Orthologous sequences are also homologous sequences.

PCR: polymerase chain reaction. Describes a technique in which cycles of denaturation, annealing with primer, and then extension with DNA polymerase are used to amplify the number of copies of a target DNA sequence.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the DNA, RNA, and proteins herein disclosed. Embodiments of the invention comprising medicaments can be prepared with conventional pharmaceutically acceptable carriers, adjuvants and counterions as would be known to those of skill in the art.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, ethanol, sesame oil, combinations thereof, or the like, as a vehicle. The medium may also contain conventional pharmaceutical adjunct materials such as, for example, pharmaceutically acceptable salts to adjust the osmotic pressure, buffers, preservatives and the like. The carrier and composition can be sterile, and the formulation suits the mode of administration. For solid compositions (e.g., powder, pill, tablet, or capsule forms), conventional non-toxic solid carriers can include, for example, pharmaceutical grades of mannitol, lactose, starch, sodium saccharine, cellulose, magnesium carbonate, or magnesium stearate. In addition, to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The composition can be a liquid solution, suspension, emulsion, tablet, pill, capsule, sustained release formulation, or powder. The composition can be formulated as a suppository, with traditional binders and carriers such as triglycerides.

Probes and primers: Nucleic acid probes and primers may readily be prepared based on the amino acid sequences provided by this invention. A probe is an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al., in *Molecular Cloning: A Laboratory Manual*, Cold Spring Harbor Laboratory Press (1989) and Ausubel et al., in *Current Protocols in Molecular Biology*, Greene Publishing Associates and Wiley-Intersciences (1987).

Primers are short nucleic acids, such as DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (*Molecular Cloning: A Laboratory Manual*, Cold Spring Harbor Laboratory Press, 1989), Ausubel et al., in *Current Protocols in Molecular Biology*, Greene Publishing Associates and Wiley-Intersciences (1987), and Innis et al., *PCR Protocols. A Guide to Methods and Applications*, 1990, Innis et al. (eds.), 21–27, Academic Press, Inc., San Diego, Calif. PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with its length. Thus, for example, a primer comprising 20 consecutive nucleotides of a cDNA or gene will anneal to a target sequence such as a homolog of that gene contained within a cDNA or genomic DNA library with a higher specificity than a corresponding primer of only 15 nucleotides. Thus, in order to obtain greater specificity, probes and primers may be selected that comprise 20, 25, 30, 35, 40, 50 or more consecutive nucleotides of the nucleic acid sequences herein disclosed.

The invention thus includes isolated nucleic acid molecules that comprise specified lengths of the disclosed gene sequences. Such molecules may comprise at least 20, 21, 25, 30, 35, 40, 50 or 100 or more consecutive nucleotides of these sequences and may be obtained from any region of the disclosed sequences. By way of example, the cDNA and gene sequences may be apportioned into halves or quarters based on sequence length, and the isolated nucleic acid molecules may be derived from the first or second halves of the molecules, or any of the four quarters. In particular, the DNA sequences may code for a unique portion of the protein, which has not been previously disclosed.

Purified: the term purified does not require absolute purity; rather, it is intended as a relative term. Thus, for example, a purified protein preparation is one in which the protein is more pure than the protein in its natural environment within a cell. In one embodiment, a preparation of a protein is purified such that the protein represents at least 50% of the total protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Recombining sites: Nucleic acid sequences that include inverted palindromes separated by an asymmetric sequence at which a site-specific recombination reaction can occur. In one specific, non-limiting example, a recombining site is a Lox P site (see above). In another specific non-limiting example, a recombining site is a Flt sites. The FRT consists of two inverted 13-base-pair (bp) repeats and an 8-bp spacer that together comprise the minimal FRT site, plus an additional 13-bp repeat which may augment reactivity of the minimal substrate (e.g. see U.S. Pat. No. 5,654,182). In other, specific non-limiting examples, a recombining site is a recombining site from a TN3, a mariner, or a gamma/delta transposon.

Recombinase: A protein which catalyses recombination of recombining sites (reviewed in Kilby et al., TIG, 9, 413–421 (1993); Landy, Current Opinion in Genetics and Development, 3, 699–707 (1993); Argos et al., EMBO J., 5, 433–440 (1986)). One specific, non-limiting example of a recombinase is a Cre protein. Another specific, non-limiting example a recombinase is a Flp protein. Other specific, non-limiting examples of a recombinase are Tn3 recombinase, the recombinase of transposon gamma/delta, and the recombinase from transposon mariner.

The Cre and Flp proteins belong to the lambda, integrase family of DNA recombinases. The Cre and Flp recombinases show striking similarities, both in terms of the types of reactions they carry out and in the structure of their target sites and mechanism of recombination (see, e.g., Jayaram, TIBS, 19, 78–82 (1994); Lee et al., J. Biolog. Chem., 270, 4042–4052 (1995)). For instance, the recombination event is independent of replication and exogenous energy sources such as ATP, and functions on both supercoiled and linear DNA templates.

The recombinases exert their effects by promoting recombination between two of their recombining sites. In the case of Cre, the recombining site is a Lox site, and in the case of Flp the recombining site is a Frt. Similar sites are found in transposon gamma/delta, TN3, and transposon mariner. These recombining sites are comprised of inverted palindromes separated by an asymmetric sequence (see, e.g., Mack et al., Nucleic Acids Research, 20,4451–4455 (1992); Hoess et al., Nucleic Acids Research, 14, 2287–2300 (1986); Kilby et al., supra). Recombination between target sites arranged in parallel (i.e., s-called "direct repeats") on the same linear DNA molecule results in excision of the intervening DNA sequence as a circular molecule. Recombination between direct repeats on a circular DNA molecule excises the intervening DNA and generates two circular molecules. Both the Cre/Lox and Flp/Frt recombination systems have been used for a wide array of purposes such as site-specific integration into plant, insect, bacterial, yeast and mammalian chromosomes has been reported (see, e.g., Sauer et al., Proc. Natl. Acad. Sci., 85, 5166–5170 (1988)). Positive and negative strategies for selecting or screening recombinants have been developed (see, e.g., Sauer et al., J. Mol. Biol., 223, 911–928 (1992)). The use of the recombinant systems or components thereof in transgenic mice, plants and insects among others reveals that hosts express the recombinase genes with no apparent deleterious effects, thus confirming that the proteins are generally well-tolerated (see, e.g., Orbin et al., Proc. Natl. Acad. Sci., 89, 6861–6865 (1992)).

Sample: Includes biological samples containing genomic DNA, RNA, or protein obtained from body cells, such as those present in peripheral blood, urine, saliva, tissue biopsy, surgical specimen, amniocentesis samples and autopsy material.

Selectable Marker: A polypeptide used to identify a cell of interest that express the polypeptide. A selectable can be detected using any method known to one of skill in the art, including enzymatic assays, spectrophotometric assays, antibiotic resistance assays, and assays utilizing antibodies (e.g. ELISA or immunohistochemistry). Specific non-limiting examples of a selectable maker are luciferase, green fluorescent protein (GFP), or beta-galactosidase. In one embodiment, a selectable marker is an enzyme. In another embodiment, a selectable marker is an enzyme. In further embodiment, a selectable marker is an antigenic epitope. Specific, non-limiting examples of selectable markers of use are proteins that make a cell drug resistance (e.g. zeomycin, hygromycin, tetracycline, puromycin or bleomycin resistant).

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs of the nucleic acid and protein sequences of the DICE transposons of the present invention will possess a relatively high degree of sequence identity when aligned using standard methods. This homology will be more significant when the orthologous proteins or cDNAs are derived from species which are more closely related, compared to species more distantly related.

Typically, homologs of the DICE transposomes of the present invention are at least 50% identical at the nucleotide level and at least 50% identical at the amino acid level when comparing DICE transposomes of the present invention to a homologous DICE transposomes. Greater levels of homology are also possible, for example at least 75%, 90%, 95% or 98% identical at the nucleotide level.

Methods of alignment of sequences for comparison are well known in the art. Various programs and alignment algorithms are described in: Smith & Waterman, *Adv. Appt. Math* 2:482, 1981; Needleman & Wunsch, *J. Mot. Biol.* 48:443, 1970; Pearson & Lipman, *Proc. Natl. Acad Sci. USA* 85:2444, 1988; Higgins & Sharp, *Gene,* 73:237–44, 1988; Higgins & Sharp, *CABIOS* 5:151–3, 1989; Corpet et al., *Nuc. Acids Res.* 16:10881–90, 1988; Huang et al. *Computer Appls. in the Biosciences* 8, 155–65, 1992; and Pearson et al., *Meth. Mol. Bio.* 24:307–31, 1994. Altschul et al., *J. Mol. Biol.* 215:403–10, 1990, presents a detailed consideration of sequence alignment methods and homology calculations.

The NCBI Basic Local Alignment Search Tool (BLAST) (Altschul et al. *J. Mol. Biol.* 215:403–10, 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI web site.

Homologs of the disclosed DICE transposomes amino acid sequence may possess at least 60% A, 70%, 80%, 90%, 95%, 98% or at least 99% sequence identity counted over full-length alignment with the amino acid sequence of the disclosed DICE transposomes using the NCBI Blast 2.0 gapped blastp set to default parameters. Queries searched with the blastn program are filtered with DUST (Hancock, and Armstrong, 1994, *Comput. Appl. Biosci.* 10:67–70). Other programs use SEG.

For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, 75%, 80%, 90%, 95%, 98%/, or at least 99% sequence identity. When less than the entire sequence is being compared for sequence identity, homologs will typically possess at least 75% sequence identity over short windows of 10–20 amino acids, and may possess sequence identities of at least 85% or at least 90% or 95% depending on their similarity to the reference sequence.

Alternatively, one may manually align the sequences and count the number of identical amino acids in the original sequence and a reference sequence that is compared to the original sequence. This number of identical amino acids is divided by the total number of amino acids in the reference sequence and multiplied by 100 to result in the percent identity.

One of ordinary skill in the art will appreciate that these sequence identity ranges are provided for guidance only; it is entirely possible that strongly significant homologs could be obtained that fall outside of the ranges provided. The present invention provides not only the peptide homologs that are described above, but also nucleic acid molecules that encode such homologs.

One indication that two nucleic acid sequences are substantially identical is that the polypeptide which the firs: nucleic acid encodes is immunologically cross reactive with the polypeptide encoded by the second nucleic acid.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that all encode substantially the same protein.

An alternative indication that two nucleic acid molecules are closely related is that the two molecules hybridize to each other under stringent conditions.

The present invention provides not only the peptide homologs that are described above, but also nucleic acid molecules that encode such homologs.

Subject: Living multicellular vertebrate organisms, a category which includes, both human and veterinary subjects for example, mammals, birds and primates.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transgenic Cell: Transformed cells which contain foreign, non-native DNA.

Transposable Element: Small, mobile DNA sequences that can replicate and insert copies at random sites within a chromosome. In general a transposable element has nearly identical sequences at each end, and oppositely oriented (inverted) repeats. Naturally occurring transposable elements (transposons) code for the enzyme, transposase, that catalyses their insertion. Bacteria have two types of transposons; simple transposons that have only the genes needed for insertion, and complex transposons that contain genes in addition to those needed for insertion. Eukaryotes contain two classes of mobile genetic elements; the first are like bacterial transposons in that DNA sequences move directly. The second class (retrotransposons) move by producing RNA that is transcribed, by reverse transcriptase, into DNA which is then inserted at a new site.

The term "transposable element" includes transposons and transposomes. Using the method described herein, a transposable element can be used to identify CAPs from the MHC class I or class II pathway.

Figure 7:
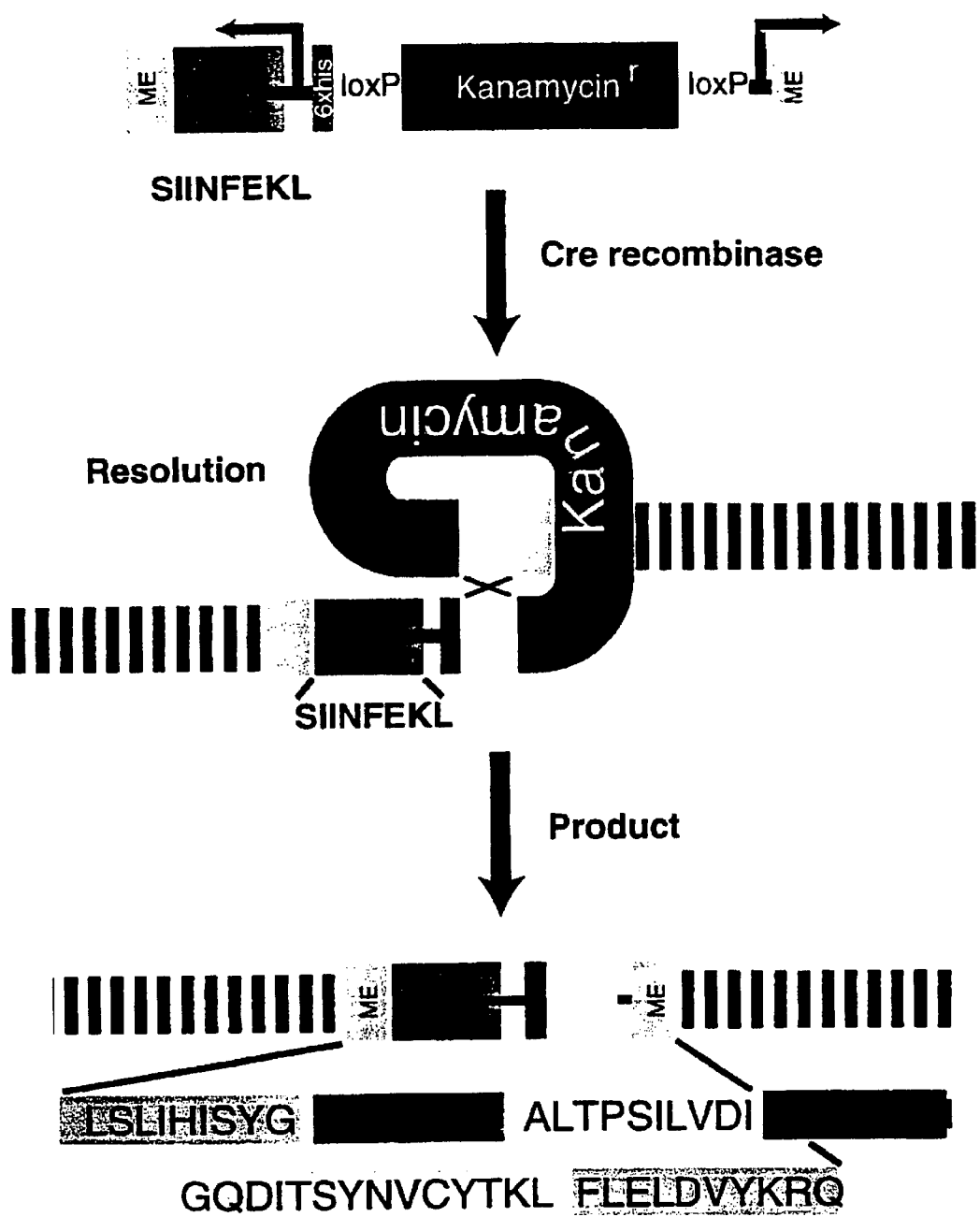
FIG. 7 is a schematic representation of a DICE I transposome, which does not contain transposase, and can be used to identify CAPs presented by the MHC I pathway.
Figure 8:
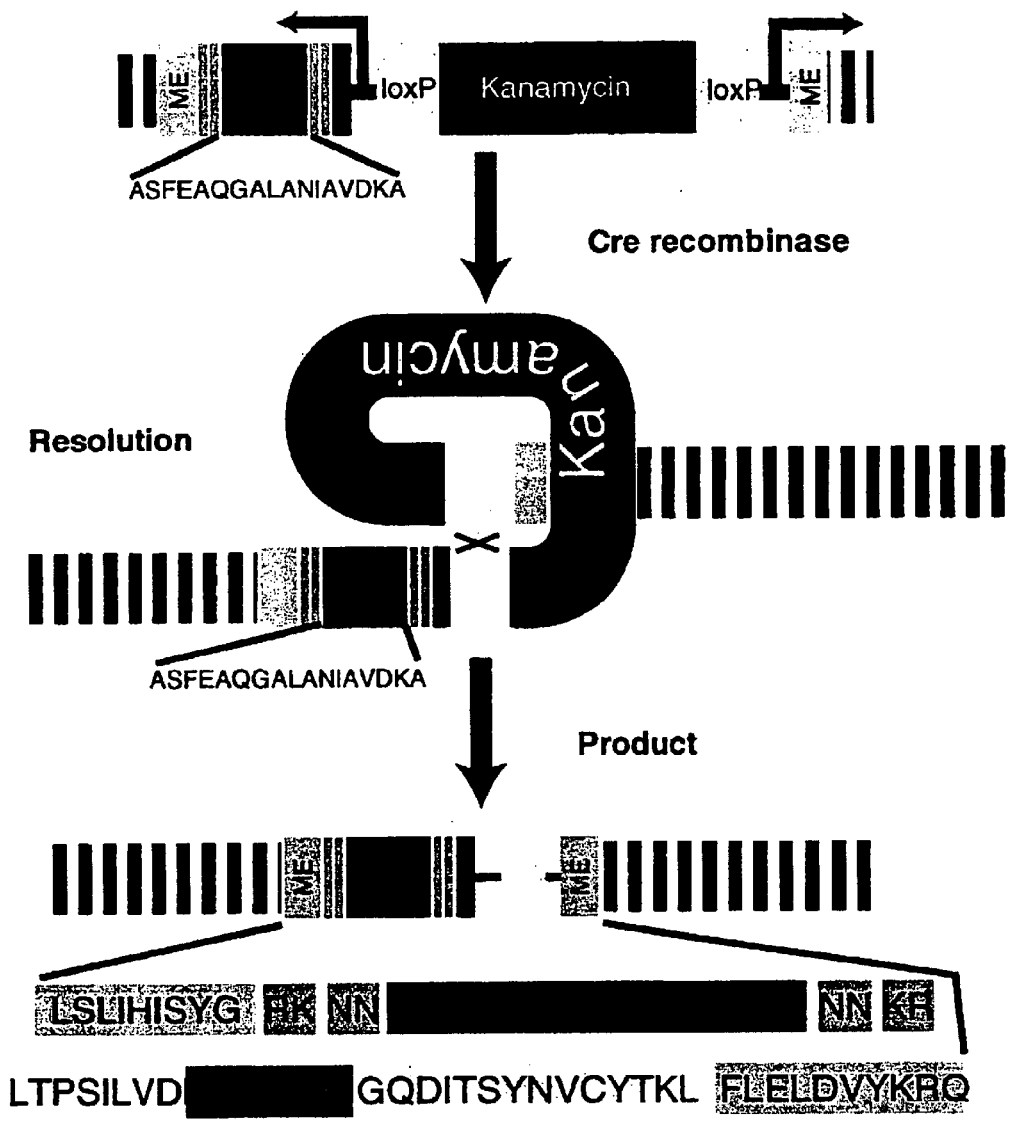
FIG. 8 is a schematic representation of a DICE II transposome, which does not contain transposase, and can be used to identify CAPs presented by the MHC II pathway.

Transposase: The enzyme responsible for transposition of transposons. As used herein, refers to both the nucleic acid sequence (e.g., see Genbank Accession No. AAB60064, and the amino acid sequence (e.g. see Genbank Accession No. U 15573) Transposome: Mobile genetic element, which is able to transport itself to other locations within a genome. As used herein, refers to a transposable element refers to a mobile genetic element which does not contain transposase. Examples include, but are not limited to DICE-I and DICE-II shown in FIGS. 7 and 8, respectively.

Transposon: A mobile genetic element, which is able to transport itself to other locations within a genome. As used herein, refers to a transposable element containing transposase. Examples include, but are not limited to Tn5-DICE shown in FIG. 2, Tn5-HER/neu/SOB shown in FIG. 5 and Tn5-HIV1/SOB shown in FIG. 6.

Vector: A nucleic acid molecule as introduced into a host cell, thereby producing a transformed host cell. A vector may include nucleic acid sequences that permit it to replicate in the host cell, such as an origin of replication. A vector may also include one or more selectable marker genes and other genetic elements known in the art.

Variants of Amino Acid and Nucleic Acid Sequences: The production of the disclosed DICE transposons can be accomplished in a variety of ways. One of ordinary skill in the art will appreciate that the DNA can be altered in numerous ways without affecting the biological activity of the encoded protein. For example, PCR may be used to produce variations in the DNA sequence which encodes the disclosed DICE transposomes. Such variants may be variants that are optimized for codon preference in a host cell that is to be used to express the protein, or other sequence changes that facilitate expression.

Two types of cDNA sequence variant may be produced. In the first type, the variation in the cDNA sequence is not manifested as a change in the amino acid sequence of the encoded polypeptide. These silent variations are simply a reflection of the degeneracy of the genetic code. In the second type, the cDNA sequence variation does result in a change in the amino acid sequence of the encoded protein. In such cases, the variant cDNA sequence produces a variant polypeptide sequence. In order to optimize preservation of the functional and immunologic identity of the encoded polypeptide, any such amino acid substitutions may be conservative. Conservative substitutions replace one amino acid with another amino acid that is similar in size, hydrophobicity, etc. Such substitutions generally are conservative when it is desired to finely modulate the characteristics of the protein. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys Leu or Ile for Met; Met, Leu or Tyr for Phe; Thr for Ser; Ser for Thr; Tyr for Trp; Trp or Phe for Tyr; and Ile or Leu for Val.

Variations in the cDNA sequence that result in amino acid changes, whether conservative or not, are minimized to enhance preservation of the functional and immunologic identity of the encoded protein. The immunologic identity of the protein may be assessed by determining whether it is recognized by an antibody to the disclosed DICE transposomes; a variant that is recognized by such an antibody is immunologically conserved. In particular embodiments, any cDNA sequence variant will introduce no more than 20, for example fewer than 10 amino acid substitutions into the encoded polypeptide. Variant amino acid sequences can, for example, be 80%, 90% or even 95% identical to the native amino acid sequence.

Conserved residues in the same or similar proteins from different species can also provide guidance about possible locations for making substitutions in the sequence. A residue which is highly conserved across several species is more likely to be important to the function of the protein than a residue that is less conserved across several species.

Additional definitions of terms commonly used in molecular genetics can be found in Benjamin Lewin, *Genes V* published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecuelar Biology and Biotechnology: a Comprehensive Desk Reference*, published by VCH Publishers, Inc., 1995 (ISBN 1-56081-569-8).

EXAMPLE 1

Generation of Transposable Elements

Transposable elements have the ability to randomly distribute MHC class I or class II epitopes throughout a bacterial genome. Transposable elements are flanked at the 5' and 3' end with insertion ends, which bind transposase. In general, insertion ends are about 19 nucleotides in length. Examples of 5' insertion ends include, but are not limited to, the I end of IS50R (see GenBank Accession No. U32991.1) and a mosaic sequence of the I and O end. Examples of 3' insertion ends include, but are not limited to, the O end of IS50R (see SEQ ID NO U00004.1) and a mosaic sequence of the I and the O end (see FIG. 10).

Transposable elements also contain a pair of recombining sites, such as pair of minimal loxP sequences, which upon interacting with a recombinase, such as a cre recombinase, allow the sequences located between the recombining sites to be removed upon insertion of the transposable element into the bacterial genome. In one embodiment, the 5' loxP sequence is located 5' to the nucleic acid sequence encoding a selectable marker and 3' to the MHC class I or class II epitope. The 3' loxP sequence is located 5' to the 3' insertion end and 3' to the nucleic acid sequence encoding a selectable marker. The loxP sequences used in the present invention (SEQ ID NO 11) contain an example of a minimal sequence which allows loxP to retain its function. Longer loxP sequences may be used in the present invention. However, a longer loxP sequence will be inserted into the bacterial genome. Without being bound by theory, a smaller insertion into the protein is more likely to allow the protein to function properly.

Transposable elements of the present invention also contain a nucleic acid sequence encoding a selectable marker, located between the loxP sequences, which allows for selection of bacteria containing the transposable element plasmid. In one embodiment, the nucleic acid sequence encoding a selectable marker encodes antibiotic resistance. The nucleic acid sequence encoding a selectable marker chosen may depend on the bacteria into which the transposable elements are inserted. For example, if *Salmonella* is used, a kanamycin resistance cassette may be used in the transposable element. Examples of other antibiotic resistance cassettes that may be used to practice the present invention include, but is not limited to ampicillin tetracycline, chloramphenicol, neomycin, hygromycin, zeocin.

MHC class I or class II restricted epitopes are delivered to a bacterial genome by the transposable elements of the present invention. The MHC epitope is located 3' to the 5' insertion end, and 5' to the 5' loxP sequence. The MHC epitope used has at least one antibody binding site available. The antibody binds preferentially to the epitope complexed with MHC molecules, not to the free epitope. Examples of class I MHC epitopes which can be used include, but are not limited to, the ovalbumin epitope, SIINFEKL (SEQ ID NO 6), and the HLA-A2 restricted human T-cell epitope LLF-GYPVYV (GenBank Accession No. B45714) from HTLV-1. Examples of class II MHC restricted epitopes which can be used include, but are not limited to, the 1-A$^b$ restricted T-cell epitope, ASFEAQGALANIAVDKA (GenBank Accession No. 228499).

Transposable elements of the present invention may also contain the Tn5-transposase sequence. If present, transposase is located 3' to the nucleic acid sequence encoding a selectable marker and 5' to the 3' lox P sequence. Upon addition of cre recombinase, the transposase and nucleic acid sequence encoding a selectable marker are removed.

The transposable elements of the present invention may be used to transpose MHC epitopes into the genome of a wide-variety of organisms, including bacteria. Examples of organisms that may be used to practice the present invention include, but are not limited to *Salmonella, Mycobacterium tuberculosis, Plasmodium*, and *Listeria monocytogenes*.

EXAMPLE 2

Construction of Tn5-Based DICE Transposable Elements

A Tn5-DICE transposon was generated which consists of a Tn5-transposase and an antibiotic resistance cassette (kanamycin) flanked at its 5' and 3' ends by direct repeats of a minimal loxP recombination site (FIG. 1). The entire Tn5-DICE transposon is flanked by the IS50R I and O ends. The 5' end of the transposon consists of the Tn5 I-end, the H-2$K^b$ restricted ovalbumin epitope SIINFEKL (SEQ ID NO 6), a 6×-histidine tag, and one loxP site, which are translationally in-frame. Tn5-DICE randomly distributes the ovalbumin epitope, SIINFEKL (SEQ ID NO 6), throughout the bacterial chromosome. Epitope-tagged CAPs released from the infecting bacteria are processed by the proteolytic machinery of the host cell and the carried the ovalbumin epitope SIINFEKL (SEQ ID NO 6), is presented in the context of H-2$K^b$ on the surface of the host cell (see FIG. 11). In this construct, the I end is amino acids 1–19, the SIINFEKL (SEQ ID NO:6) is at position 28–52, the 5' PCR site is at position 54–77, the 6×Histidine is position 82–100, the Lox P is at position 109–143, the 3' PCR end is at position 145–167, and the O end is at position 153–171 (see FIG. 12).

Tn5-DICE was constructed so that upon induction with Cre recombinase, the insertion is resolved at the loxP sites. The kanarnycin and Tn5-transposase cassettes are segregated to non-replicating loops and lost. When the insertion is in-frame to a gene, the 49 amino acid resolved product creates a fusion protein carrying the SIINFEKL (SEQ ID NO 6) epitope (FIG. 2).

An *E. coli* donor strain (ATCC; 53323), containing both an F' plasmid and the Tn5-DICE bearing plasmid, pDE510 (tra-/mob) (FIG. 3A) was mated with a nalidixic acid-resistant *Salmonella typhimurium* strain (ATCC No. 14028). The bacteria were mated by incubating together at a 1:1 ratio in Luria-Bertani broth at 37° C. for 12 hrs. Nalidixic acid and kanamycin resistant *Salmonella* transconjugants, which contain both the F' plasmid and the Tn5-DICE bearing plasmid, pDES10(F'::Tn5-DICE), were isolated. The presence of F'::Tn5-DICE was confirmed using a P22 sensitivity test (Miller J. H. Experiments in Molecular Genetics Cold Spring Harbor Laboratory Press (1972)) and by the ability to transfer the transposon kanamycin marker back into *E. coli* or *Salmonella* recipients at a frequency equal to F' plasmid transfer frequencies. This is a control experiment to insure that the insertion is truly on the F' plasmid. The F' plasmid transfers at a specific frequency. If the transposable element is carried on the F' plasmid, then it should be re-transferable to a new recipient at a rate equal to that of the initial mating.

The *Salmonella*-specific bacteriophage, P22 (HTint) (ATCC. 19585-B1), was used to make a pooled (meaning that a donor culture of *Salmonella* strains carrying the F' plasmid with the transposon insertion is used to make a phage lysate) lysate of the *S. typhimurium* transconjugants carrying F'::Tn5-DICE. P22 transduction is a frequently used method of transferring genetic markers between *Salmonella* strains. Because there is no sequence homology to F' in *Salmonella*, the P22 phage lysate was used to mutagenize a second *Salmonella* recipient (ATCC 14028), *Salmonella* strain containing pBAD33cre. The lack of F' homology in the recipient insured that kanamycin resistant transductants derived as a result of transposition rather than homologous recombination. Transductants were selected by kanamycin resistance (30 μg/ml) on Luria agar. The Cre recombinase in pBAD33cre (FIG. 3B) is under tight regulatory control of the pBAD promoter and mediates resolution and loss of the kanamycin resistance gene and the Tn5 transposase gene only when the strain is grown in the presence of arabinose (1 mM). The pBAD33cre plasmid is unstable and is lost in 3–10 generations when *Salmonella* strains bearing this plasmid are grown without selection.

The *Salmonella*-specific bacteriophage, P22 (HTint) was used to make a pooled lysate of the *S. typhimurium* transconjugants carrying F''::Tn5-DICE (a donor culture of *Salmonella* strains carrying the F' plasmid with the transposon insertion was used to make a phage lysate). Because there is no sequence homology to F' in *Salmonella*, the P22 phage lysate was used to mutagenize a second *Salmonella* recipient, *Salmonella* strain containing pBAD33cre, (ATCC 14028). The plasmid pBAD33cre was constructed as follows. Cre-recombinase was cloned by PCR amplification from the cre-recombinase expressing *Eschericia coli* strain NS2114 (Seifert, et al., Proc. Natl. Acad. Sci. 83:73540 (1986)). A ClaI-HindeIII digest of the sub-cloned cre-recombinase gene was cloned into a ClaI-HindeIII digest of the arabinose-inducible plasmid pBAD33 (Guzman, et al., J. Bacteriol. 177(14):4121–30 (1995)). The lack of F' homology in the recipient insured that kanamycin resistant transductants derived as a result of transposition rather than homologous recombination. Transductants were selected by kanamycin resistance (30 μg/ml) on Luria agar. The Cre recombinase in pBAD33cre (FIG. 3B) is under tight regulatory control of the pBAD promoter and mediates resolution and loss of the kanamycin resistance gene and the Tn5 transposase gene only when the strain is grown in the presence of arabinose (1 mM). The pBAD33cre plasmid is unstable and is lost in 3–10 generations when *Salmonella* strains bearing this plasmid are grown without selection.

EXAMPLE 3

Identification of Strains Containing DICE Insertions

The pool of *S. typhimurium* mutants generated in EXAMPLE 1 was enriched for in-frame insertions of the resolved Tn5-DICE transposon within genes encoding secreted effector proteins by fluorescence activated cell sorting (FACS). If Tn5-DICE were randomly integrated, approximately ⅙ (20,000) mutants of the 120.000 independent Tn5-DICE insertions generated should contain resolved in-frame insertions. Of these, many insertions will be in metabolic genes that may be essential. In addition, many insertions will be in promoter or non-coding intergenic regions. Of the remaining mutants, far fewer will be contained within CAPs. The precise number of CAPs in *S. typhimurium* is unknown. Since DICE insertions within CAPs may be rare events, a sensitive selection procedure was required. With the appropriate cell marker, FACS enabled the isolation of extremely rare mutants.

Infection of Macrophages

Femurs were harvested from 4–6 week old C57B1/6 mice (H-2 Kb). Bone marrow cells were extracted by ravaging each end of the femur with a 3 cc syringe containing a 30 gauge needle and 2 mls of RPMI. The bone marrow cells were washed three-times with RPMI at 37° C. and resuspended at 1×10' cells/ml in RPMI 1640/10% EBS containing 20% L929 media as a source of Granulocyte Macrophage Colony Stimulating Factor (GM-CSF). L929 media was derived by growing L929 cells (murine fibrosarcoma, American Type Culture Collection, Mannassas, Va.) and subsequently harvesting the media seven days after growing cells to confluence. The cultures differentiated into bone marrow derived macrophages (BMDM) by culturing the bone marrow cells for six days at 37° C., 5% $CO_2$. BMDM were resuspended in RPMI 1640/10% FBS and seeded into 6-well plates at $1\times10^7$ cells per well.

The pooled Tn-5 resolved SIINFEKL (SEQ ID NO 6) library (*S. typhimurium*) generated in EXAMPLE 1 was used to infect BMDM cells. An extensive library of independent insertions of the Tn5-DICE transposon was generated to insure that each gene encoded by *S. typhimurium* received multiple "hits." The pooled library was grown overnight in Luria broth (LB) at 37° C. with shaking. The pooled library was washed three-times in RPMI 1640 and suspended in RPMI at $5\times10^8$ cells/ml. The resuspended library (20 μl) was dispensed into individual wells containing adhered BMDM cells (MOI=1). A MOI of one or less limits multiple infections within the same BMDM. A 1% infection rate is expected for *S. typhimurium* in vitro. Cultures were centrifuged for two minutes at 200 rpm to initiate contact and subsequently incubated at 37° C. for one hour. The cultures were washed three times with 37° C. phosphate buffered saline (PBS, pH 7.4,9 g/l NaCl; 0.144 g/l $KH_2PO_4$; 0.795 g/l $Na_2HPO_4$). The cultures were overlayed with three mls of RPMI 1640/10% FBS containing 50 μg/ml gentamycin to kill extracellular bacteria, then incubated at 37° C. for two hours. The cultures were washed three times with 37° C. PBS and the cells scraped from the plate, resuspended in 10 mls of RPMI 1640/1% FBS, and incubated on ice.

FACS Analysis

The BMDM cells were incubated with FITC-conjugated anti-H-2 $D^b$ and biotinylated anti-H-2 $K^b$/SIINFEKL (5 μg 25-D1.2). The H-2/$K^b$/SIINFEKL-specific antibody (25-D1.2) was available from R. Germain, National Institutes of Health. The I-Ab ASFEAQGALANIAVDKA -specific antibody (Y-ae) was a gift from Dr. Leszek Ignatowicz at the Institute of Molecular Medicine and Genetics, Medical College of Georgia, Augusta, Ga.). Cells were labeled with antibody for 30 min at 4° C. Anti-H-2 $K^b$/SIINFEKL, a monoclonal antibody only recognizes the SIINFEKL epitope (SEQ ID NO 6); Porgador, et al., Immunity 6(6): 715–26 (1997)) when it is complexed with the class-I restrictive element H-2 $K^b$. Since neither BMDM cells nor wild-type *Salmonella* manufacture this peptide, the infecting *Salmonella* strain containing the resolved insertion is the source of the (SEQ ID NO 6) epitope. Cells were washed three-times in 4° C. PBS and incubated with one μg phycoerythrin (PE) conjugated streptavidin (Caltag).

FACS analysis was used to identify and isolate *Salmonella*-infected macrophages that contained in-frame resolved transposon insertions within genes having access to the class-I antigen processing and presentation pathway of the macrophage. BMDM infected with the *Salmonella*-DICE library were sorted by first gating on the forward and side scatter population characteristic for macrophages. Bright red (PE-anti-H-2 $K^b$/SIINFEKL) and bright green (FITC-conjugated anti-H-2 $D^b$) populations, visualized in the double positive quadrant, were sorted into a five ml polypropylene tube containing two mls of RPMI 1640/1% FBS. The sorted cells were centrifuged, lysed in LB/1% Triton X-100, then plated on LB agar and incubated at 37° C. overnight to recover *Salmonella*-DICE strains.

Infected BMDMs lacking CAP insertions can be recovered as a consequence of aggregate formation in the flow sorted population. To ensure that recovery was due to phenotypic expression of H-2 Kb/SIINFEKL, the recovered bacterial colonies were counted, pooled, and subjected to two additional rounds of FACS sorting to enrich for *Salmonella* mutants containing CAP insertions. Individual isolates were subjected to an additional round of FACS analysis to confirm their phenotype. *Salmonella* infecting the double positive BMDM were removed and grown for confirmation and sequencing.

EXAMPLE 4

Sequencing of CAP Genes

Figure 4:
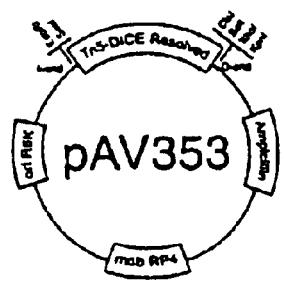
FIG. 4 is a schematic representation showing one embodiment of the method developed to sequencing the Tn5-DICE-resolved CAPs. A. Suicide plasmid pAV353, containing a resolved copy of Tn5-DICE, was conjugated into a naladixic acid resistant, Cre expressing Tn5-DICE mutant B. An ampicillin and naladixic acid resistant transconjugant was obtained via Cre-loxP recombination. C. Isolated chromosomal DNA was restricted with EcoRI or SalI to clone 5'- or 3'-sequences flanking the original SIINFEKL inaction, respectively.
Figure 4:
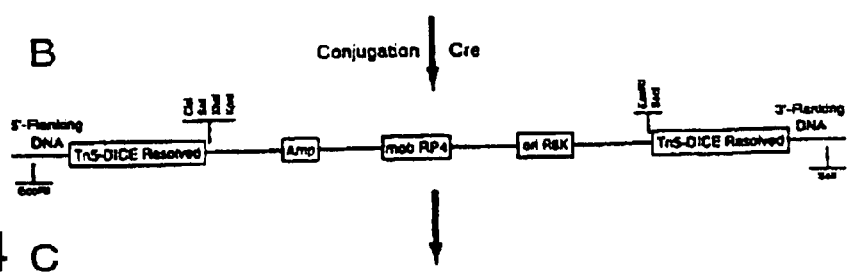
Figure 4:
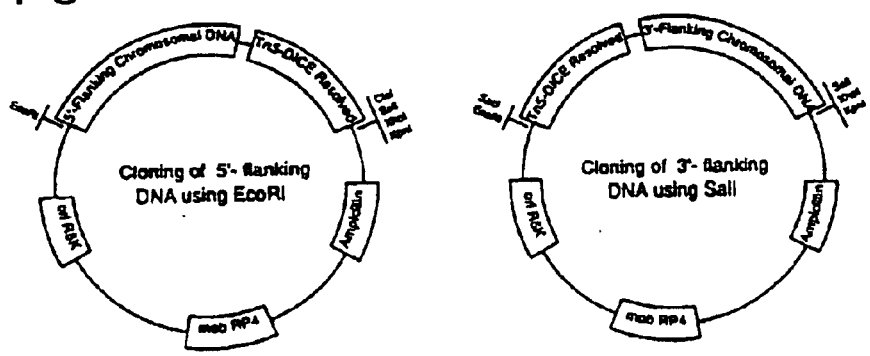

To determine the identity of CAPs containing in-frame SIINFEKL (SEQ ID NO 6) insertions, a unique system allowing specific and efficient identification of CAP genes was developed (FIG. 4). The system was also used to efficiently retransduce Tn5-DICE mutants and reconfirm their phenotypes. A KpnI-SacI fragment of a plasmid carrying the resolved Tn5-DICE transposon (pAV353a) was cloned into an ampicillin-resistant suicide vector, pGP704, to yield plasmid pAV353 (FIG. 4A).

Plasmid pAV353 (amp' tra$^+$ mob*) was transformed into *E. coli* S17 λpir (Kinder, S. A. et al. Gene 136, 271–5 (1993)an ampicillin resistant, nalidixic acid sensitive donor strain, and conjugated into spontaneous naladixic acid resistant, Cre expressing *S. typhimurium* Tn5-DICE mutant CAP mutants containing pBAD33cre. Transconjugants (amp' nal') carrying an integrated copy of plasmid pAV353 at the chromosomal loxP site were selected following induction of the Cre recombinase, by selecting naladixic acid and ampicillin resistant transconjugants (FIG. 4B).

Chromosomal DNA was isolated, digested for 2 hours at 37° C. with one of several possible restriction endonucleases (see FIG. 4A), to allow cloning of either 5'- or 3'-DNA sequences flanking the original SIINFEKL (SEQ ID NO 6) insertion. Digested DNA was absorbed over a DNA purification column to remove the restriction endonuclease, and ligated overnight at 15° C. Ampicillin resistant transformants were further analyzed using Tn5-DICE specific primers 5'GCGGATATCCACCACCACCACC-3' (ClaI, SalI, XhoI, or KpnI digests) or 5'-TATGCCCGGGCCG-TGGTGGTGG-3' (EcoRI, SacI digests).

Upon transformation into *E. coli* S17λpir, re-ligated circular fragments containing pAV353 form functional replicons resulting in ampicillin-resistant transformants. Re-ligated chromosomal fragments carrying the integrated plasmid pAV353 form functional replicons in E. coli S17 λpir and carry either 3'-(i.e. SalI) or 5'-(i.e. EcoRI) sequences flanking the original SIINFEKL (SEQ ID NO 6) insertion (FIG. 4C). Ampicillin-resistant transformants were further analyzed using Tn5-DICE specific primers 5'-GCGGATATCCACCACCACCACC-3' (ClaI, SalI, XhoI, or KpnI digests) (SEQ ID NO 1) or 5'-TATGCCCGGGCCGTGGTGGTGG-3' (EcoRI, SacI digests) (SEQ ID NO 2).

As shown in Table 1, the Tn5-DICE transposon (FIG. 2) enabled the identification of class-I-MHC-accessible S. typhimurium proteins in both macrophages and an intestinal epithelium cell line (see EXAMPLE 4). S. typhimurium proteins not predicted to reach the class I pathway of the host cell were identified. In addition, in at least one instance, a bacterial effector protein unique to S. typhimurium secreted into the cytoplasm of the host cell has been identified (LS28). Characterization of the immune response to each CAP identified may enable the construction of highly specific carrier vaccines, allowing immune responses to be tailored to the life cycle of specific pathogens.

TABLE 1

Salmonella genes identified by DICE

| Strain | Gene | Comp.* | Bacteria | CMT-93 | Function/Homology |
|---|---|---|---|---|---|
| LS28 | ams** | S | S. t., S. typhi | + | Protease IV |
| SIIN16 | argT | P | S. t., S. typhi, E. c. | − | Arginine Transport |
| SIIN17 | fhuA | P | S. t., S. typhi, E. c | − | Iron Transport |
| SIIN27 | S2OMP | OMP | S. t., S. typhi, E. c, K. p. | − | Outer Membrane Protein |
| SIIN15 | htpG | S? | S. t., S. typhi, E. c | + | High Temperature Heat Shock Protein |
| SIIN29 | hemK | C | S. t., S. typhi, E. c | − | Heme Biosynthesis |
| SIIN50 | ims75 | S | S. t., S. typhi | + | impaired macrophage survival, MIP |
| SIIN61 | ORF | S | S. t., S. typhi | + | Unknown |
| SIIN71 | hemL | C | S. t., S. typhi, E. c | − | Heme Biosynthesis |

S. t. = Salmonella typhimurium; S. typhi = Salmonella typhi; E. c. = E. coli

EXAMPLE 5

Confirmation of the DICE Method

To confirm the validity of the DICE screen, several studies were performed to insure that the CAP epitope identified was present on the surface of the antigen presenting cell (APC) and that mutants were able to stimulate T-cell specific immunity. In addition, the route of antigen delivery was investigated to determine if proteins delivered by DICE mutants were accessible to the class-I MHC pathway by an alternate antigen processing and presentation pathway or directly into the endogenous pathway by translocation across the phago-lysosomal barrier.

Fluorescence Microscopy

The Salmonella DICE strain LS28 was transfected with a plasmid which constitutively expresses green fluorescence protein (GFP). This strain (LS28GFP) of a resolved S. typhimurium/SIINFEKL was used to infect H-2 $K^b$ restricted BMDM in vitro and then fluorescently labeled using the monoclonal antibody 25-D1.2 using the methods described in EXAMPLE 2. The infected BMDM cells were imaged using wide field fluorescence imaging. H-2 $K^b$/SIINFEKL complexes were observed on the cell surface, demonstrating that BMDM derived the SIINFEKL epitope (SEQ ID NO 6) from LS28GFP.

To examine the route of antigen processing, several of the isolated DICE mutants were used to infect the H-2$K^b$ restricted murine intestinal epithelial line CMT-93 (ATCC, Manassas, Va. catalog number CCL-223). CMT-93 cannot present antigen delivered by Salmonella when the ovalbumin epitope is expressed intracellularly within the bacteria, suggesting that CMT-93 cells do not contain an alternate antigen processing pathway. The most likely explanation for CMT-93 presentation of SIINFEKL (SEQ ID NO 6) on its cell surface is that the epitope was delivered directly to the endogenous pathway as a fusion with a type III secreted protein.

The H-2 $K^b$/SIINFEKL specific CD8$^+$ T-cell hybridoma B3Z (Karttunen, et al., Proceedings of the National Academy of Sciences 89:6020–24 (1992)) is a reporter cell which turns blue when it encounters its ligand. B3Z was used as an indicator of the presence of the H-2 $K^b$/SIINFEKL complex on the surface of CMT-93. The presence of blue B3Z cells indicates that the H-2 $K^b$/SIINFEKL complex is recognized by a specific T-cell receptor and is delivered by a bacterial protein.

Monolayers of CMT-93 cells (3×10$^4$ cells/well) were infected with LS28 at an MOI of 1 in a 96 well tissue culture plate. Cultures were incubated at 37° C. for one hour, washed of non-invasive Salmonella, and overlayed with fresh media containing gentamycin (50 μg/ml). The cultures were overlayed with 3×10$^4$ cells/well of B3Z cells and centrifuged to initiate cell-to-cell contact. The cultures were incubated at 37° C. for six hours, then each well was washed, fixed (2% formaldehyde/0.2% glutaraldehyde) and incubated in developing buffer (1 mg/ml X-gal; 5 mM $K^3Fe(CN)_6$; 5 mM $K_4Fe(CN)$, $3H_2O$; 2 mM $MgCl_2$). The cells were imaged using light microscopy. The presence of blue B3Z cells indicates that the SIINFEKL epitope is being targeted directly to the cytoplasm of the host cell. This data is significant because it indicates that Salmonella is using a translocation apparatus to target these proteins into the cytoplasm. These data indicate that access to the class-I MHC pathway by Salmonella is cell type dependent.

To confirm that the stimulation of B3Z was specific (stimulation of T-cell specific immunity only when B3Z encounters CMT-93 cells infected with Salmonella), similar experiments were performed using wide-field fluorescence microscopy to visualize the CMT-93:B3Z interaction. CMT-93 cells (2×10$^5$/well, chambered coverglass #1.5) were infected with LS28GFP (37° C., 1 hour, MOI=10), overlayed with media containing gentamycin (50 μg/ml). The cultures were seeded with B3Z T-cell hybridomas (2×10$^5$ cells) and incubated at 37° C. for 12 hours. The cultures were washed three-times with PBS, fluorescent stained for cell membranes (TMA-DPH, Molecular Probes) and β-galactosidase ($C_{12}$FDG, Molecular Probes), and visualized on an Advanced Precision Instruments deconvolution microscope. Stimulation of B3Z was due to cognate interaction of B3Z with infected CMT-93. The results provide visual evidence of bacterial protein translocation. These results demonstrate that DICE analysis can be used to isolate proteins having direct access to the class-I MHC pathway of the host cell, which is cell type specific. In addition, DICE strains stimulate a specific T-cell response, due to the presence of the DICE strain.

β-galactosidase Assay

The ability of infected cells to present antigen to a T-cell reporter was also assayed using a β-galactosidase assay. The T-cell reporter is a T-cell hybridoma (a fusion between a T-cell and a tumor cell) that recognizes the SIINFEKL epitope when presented in the context of the class I MHC allele H-2K$^b$. When the T-cell encounters the SIINFEKL/ H-2 K$^b$ complex, it initiates synthesis of β-galactosidase. When incubated in the presence of a substrate (X-gal), the cell turns blue. The cell will turn blue only if this specific interaction has occurred. H-2 K$^b$-restricted epithelial cells (ATCC No. CCL-223) were infected with several *Salmonella* strains isolated by flow cytometric analysis using the methods described above in EXAMPLE 2. The cells were then infected with $1 \times 10^7$ CFU (MOI=100) of each of several DICE mutants isolated as in EXAMPLE 2. After 1 hr at 37° C., the wells were washed 3× with phosphate buffered saline (PBS) and overlayed with $1 \times 10^5$ B3Z cells. Cell to cell contact was initiated by centrifuging at 200×g for 2 minutes. The cultures were incubated at 37° C./5% $CO_2$ for 6 hrs. The cells were washed 3× with PBS and fixed in a solution of PBS containing 1% formaldehyde and 0.2% glutaraldehyde for 5 minutes at 4° C. The cells were then overlayed with a solution of PBS containing 1 mg/ml X-gal, 5 mM potassium ferricyanide, 5 mM potassium ferrocyanide, and 2 mM $MgCl_2$. The cells were allowed to incubate at 37° C. overnight and examined microscopically for the presence of blue cells.

Several of the *Salmonella* clones turned blue, demonstrating that the SIINFEKL epitope is actively directed across the phagolysosomal border by *Salmonella* after infection and is processed into the class I MHC pathway.

EXAMPLE 6

In Vivo T-cell Immunity

Access to the endogenous pathway of the host cell infers access to the class-I MHC processing and presentation pathway of the host. Vaccines that carry antigens within CAPs should be able to stimulate antigen-specific cell-mediated immune responses. In vivo T-cell immunity to these antigens is the best measure of the ability of these vaccines to stimulate appropriate responses.

C57B1/6 mice were orally immunized with several DICE strains. Briefly, female C57B1/6 mice (6–8 weeks old) were immunized by oral gavage with $1 \times 10^7$ CFU of each *Salmonella* DICE mutant.

The ability of these strains to stimulate T-cell responses in vivo can be assessed by traditional CTL assays, H-2 K$^b$/SIINFEKL tetramer analysis (using K$^b$/SIINFEKL tetramers obtained from the NIH AIDS Reagent Program), and tumor protection assays. This combination of measurements of T-cell immunity is used to confirm both the stimulation of antigen-specific T-cell populations and whether these T-cells are functional. The H-2K$^b$/SIINFEKL tetramers provide an extremely sensitive method of assessing the effect of vaccination upon the T-cell population in the immunized animal. A positive effect would be manifested by an increase in total antigen-specific T-cells after immunization. An increase in antigen-specific T-cells following immunization however tells little about the functionality of these cells. If you have stimulated an antigen-specific population by immunization, the vaccine would be poorly constructed if the stimulated cells could not kill their targets. The CTL assays provide a necessary and accurate measure of the functionality of the antigen-specific T-cell population. Tumor cells which express the SIINFEKL epitope are used as targets for the assay. If the vaccine stimulates an antigen-specific T-cell population and these cells are able to efficiently kill their targets, then the vaccine can be considered to effectively engender a protective immune response.

EXAMPLE 7

Construction of a Heterologous Antigen Breast Cancer Vaccine

The transposable elements of the present invention allow for rapid identification of CAPs, which may serve as beneficial targets for vaccine development. Since CAPs have access to the host immune system, vaccines against viruses, bacteria, and cancer can be constructed using CAPs as vaccine carriers that target protective epitopes (for example pieces of proteins from foreign infectious agents or cancer cells) directly to the cytoplasmic compartment of APCs. Access to the class I or class II pathway of the host cell indicates that many proteins may serve as attractive vaccine targets. Heterologous antigen expressed by *Salmonella* vaccine strains may induce a protective immune response in animals and humans. Heterologous antigen-specific immunity can consist of both local and systemic Th1 or Th2 type immune responses.

HLA-A2-restricted epitopes derived from HER2/neu deposited directly into the cytoplasmic compartment of the APC by CAPs may result in better MHC class I presentation, thus greatly enhancing induction of cell-mediated immunity. Her2/neu is an epidermal growth factor-like protein whose upregulation is associated with a variety of cancers of the breast and other tissues. Engendering a strong and persistent cellular immune response is essential for protective immunity to tumors such as HER2/neu-elevated breast cancer. This example describes the construction and delivery of HER2/neu/SOB (HER2/neu/String of Beads) insertions throughout the chromosome of *S. typhimurium*, using a variant of the Tn5-DICE transposon shown in FIG. 2.

HER2/neu/SOB Library Construction

Figure 5:
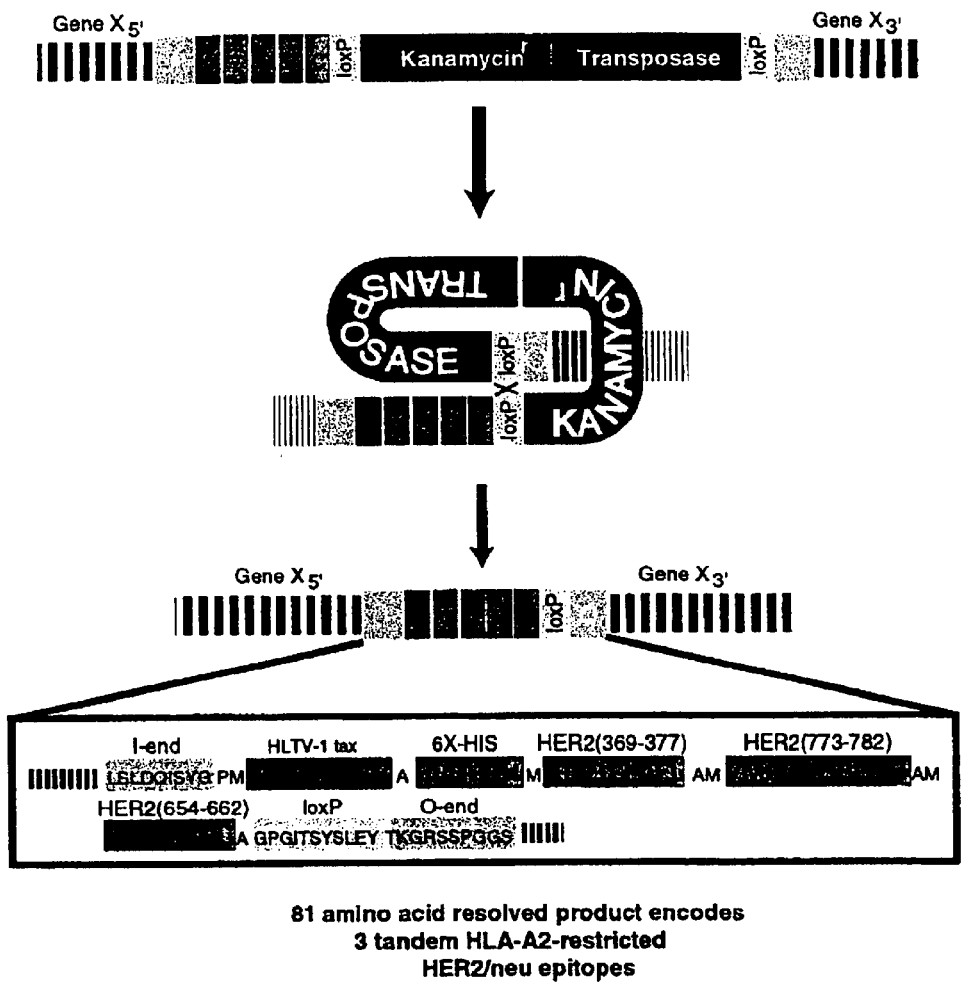
FIG. 5 is a schematic representation showing the Tn5-HER2/neu/SOB (HER2/neu/String of Beads) construct.

A transposon system was developed to generate a library of epitope insertions containing the HLA-A2-restricted HER2/neu epitopes (FIG. 5). HER2/neu/SOB carries a 6×-histidine site, the HLA-A2-restricted HTLV-1 tax epitope LLFGYPVYV and three HLA-A2 restricted HER2/ neu epitopes HER2/neu$_{(369-377)}$, HER2/neu$_{(773-782)}$, and HER2/neu$_{(654-662)}$. Resolved in-frame insertions of Tn5-HER2/neu/SOB creates an 81 amino acid product encoding each epitope.

Initially, wild-type *S. typhimurium* (strain 14028s) is used to avoid possible interaction between the attenuating mutation and the DICE insertions. The DICE insertion in the strains that present antigen best are transduced into, for example, three other strain backgrounds to test their immune response in HLA-A2.1 transgenic mice. Attenuated strains will contain mutations in aroA. AroA is an enzyme involved in the biosynthetic pathway for Aromatic amino acids. Mutations in the aroA locus severely attenuate *Salmonella* vaccine strains thereby diminishing the ability of the vaccine strain to disseminate and cause disease. Alternatively, attenuated strains CL401 or CL553 can be used (two *Salmonella typhimurium* strains shown in our lab to be severely attenuated for virulence. The location of the mutations are unknown). aroA can be used because mutations in aromatic amino acid biosynthesis are used in CV908 (a *Salmonella typhi* vaccine strain) that appears to be one of the best *S. typhi* vaccines.

Using the methods described above in EXAMPLES 1–3, P22, is used to make a lysate of the *Salmonella* strain containing F'::HER2/neu/SOB. The pool of S. typhimurium mutants are enriched for in-frame insertions of the HER2/neu/SOB cassette within CAPs by FACS as described above, with modifications noted below.

Identification of Salmonella Isolates Able to Facilitate HTLVItax Class I Presentation Salmonella SOB-containing proteins that direct peptides into the class I pathway from a library of Salmonella strains which contain the SOB peptide can be identified using a monoclonal antibody specific to HTLVItax/A2.1.

BMDM isolated from H-2$K_b$/HLA-A2* transgenic mice (C57B1/6 background) are seeded onto 6-well tissue culture plates ($1\times10^7$ cells/well) and infected with the pooled *S. typhimurium*/HIV-1/SOB library (37° C., MOI=10). After one hour, the cells are washed, overlayed with RPMI 1640/10% FBS (gentamycin, 50 $\mu$g/ml), and incubated for 2 hours (37° C.). The cells are harvested, washed, and suspended in 10 ml RPMI 1640/1% FBS. The BMDM are labeled with FITC-conjugated anti-H-2 $D^b$ (Caltag) and biotinylated A6-TCR chimeric antibodies (a chimeric antibody which recognizes HLA-A2 complexed with the HTLV-Itax epitope LLFGYPVYV (obtained from Dr. Jonathan Schneck, Johns Hopkins University; O'Herrin, et.al., Journal of Experimental Medicine 186(8): 1333–45)to tag class I-expressing cells presenting the ta peptide in the context of HLA-A2. The biotinylated A6-TCR is subsequently labeled with PE-streptavidin (Caltag). The BMDM are re-suspended in RPMI 1640/1% FBS (4° C.) and sorted using FACS analysis by gating on populations expressing both H-2 $D^b$ and A6-TCR Bacteria recovered from the sorted cells, are pelleted and lysed in LB broth containing 1% triton X-100 followed by plating on LB-agar as described above in EXAMPLE 2.

To identify the gene carrying the in-frame HER2/neu/SOB insertion, a DNA template for sequence analysis is generated using a variation of the TAIL PCR method (see EXAMPLE 3). This method employs the use of sequential, tandem oligonucleotides that prime within the resolved HER2/neu/SOB insertion and amplifies epitope insertions thus identifying the region flanking the insertion. The entire cycling procedure is performed sequentially as a series of primary, secondary and tertiary reaction conditions. The primary and secondary conditions are performed in volumes of 100 $\mu$l. All cycling conditions are as published (Liu and Whittier, 1995). Briefly, This method utilizes a complex array of melting and annealing procedures to determine the sequence flanking the insertion. To accomplish this, three tandem primers are used to "walk" down the insertion and amplify from a fourth random primer. After amplification, the fragment is gel purified and cloned into a sequencing vector.

Alternatively, chromosomal preparations are made from each isolated bacterium containing a CAP insertion. 1 $\mu$g of the chromosome is digested with the restriction enzyme pstI for 1 hr at 37° C. and then purified. The chromosome is then ligated by the addition of ligase overnight at 15° C. The circularized mix is then subjected to inverse PCR using the primers CTACTAGTATGGATGGTGTC and CTAGAACCAGAT GTGTATAAG. The PCR mix is as follows: 1 mM each primer, 10 ng template, 0.2 mM dNTP (dATP, dCTP, dGTP, dTTP), 0.5 Taq polymerase, 10 $\mu$l 10×PCR buffer, 1 mM $MgCl_2$, and $H_2O$ to 100 $\mu$l. Cycling conditions are melting: 95° C., 30s; annealing: 55° C., 1 min; extension: 72° C., 3 min; 35 cycles.

EXAMPLE 8

Characterization or Heterologous Antigen Breast Cancer Vaccines

After the construction of the *S. typhimurium*/HER2/neu vaccine strain described in EXAMPLE 7, the ability of the vaccine to induce epitope-specific, cell-mediated immune responses in HLA-A2 transgenic mice is characterized and quantified. An advantage of the *Salmonella* vaccine system is that there is a relevant small animal model, the mouse, in which to evaluate the safety and efficacy of the vaccine constructs developed.

Vaccine candidates can be chosen based upon criteria such as: 1) genes encoding CAPs proteins must be conserved between *S. typhimurium* and *S typhi* (as judged from the *Salmonella* genome projects); and 2) CAPs carrying epitope insertions must be recoverable upon repeated independent flow sorts. In previous experiments, all strains containing gene insertions that resulted in presentation of SIINFEKL in H-2$K^b$ were recovered a second time. Other criteria may also be used.

*S. typhimurium* HER2/neu/SOB vaccine strains isolated in EXAMPLE 7 are used to orally immunize $K^b$/HLA-A2 transgenic mice. The mice were immunized by oral gavage with $1\times10^7$ infectious units of *Salmonella*. The response generated from each vaccine is subsequently analyzed using the following methods.

HLA-Tetramer Construction and Analysis of Epitope-Specific T-Cells

The T-cell response to vaccination may, for example, be initially assessed by HLA-tetramer analysis of T-cell populations derived from the spleens and mesenteric lymph nodes of vaccinated, sham vaccinated, and unvaccinated HLA-A2 transgenic mice. The HLA-A2 transgenic mice utilized were from Dr. Linda Sherman, Scripps Institute, LaJolla, Calif. To assess the class I response to each HER2/neu epitope, HLA-A2 tetramers containing each HER2/neu epitope plus one irrelevant control are used. HLA-A2 and β2-microglobulin expressing plasmids can be obtained from Dr. John Altman, Emory University. Conversely, tetramers are available from the Aids Reagent Repository at the National Institutes of Health, Bethesda Md. Freshly isolated spleen cells and cells derived from mesenteric lymph nodes from $K^b$/HLA-A2 mice immunized with each *S. typhimurium* HER2/neu/SOB vaccine are labeled with FITC-conjugated anti-CD8 and each respective PE labeled HLA-A2 tetramer. Specifically, 1×106 cells are labeled with 1 $\mu$g of each respective tetramer and 5 $\mu$g of anti-CD8 antibody for 30 min at 4° C. The effector status of the tetramer positive CD8 populations are further characterized by assessing the level of expression of CD28, CD44, and CD62. These markers are hallmarks of the state of differentiation of the effector cells. Each cell population will be labeled with 1 $\mu$g of each respective marker for 30 min at 4° C. The $CD8^+$/CD44lo/$CD62^+$ phenotype correlates with a memory population of splenic effector cells. From this data, the nature of the cellular response to vaccination is characterized. Ideal vaccine candidates should yield a strong memory CTL population that is capable of rapid upregulation after restimulation by the infectious agent the vaccine was designed for.

CTL Lysis of HIV Epitope Expressing Targets

Epitope-specific T-cells resulting from vaccination of $K^b$/HLA-A2 transgenic mice with tumor epitopes are capable of mediating killing of human HLA-$A2^+$ tumor targets. To assess the ability of *Salmonella* vaccine strains to generate HER/neu-specific CTLs, assays designed to measure the lytic capacity of the CTL population generated as a result of vaccination can be used. To measure specific immune response to HER2/neu, a chromium release assay can be used to measure the ability of CTLs generated in vaccinated mice to kill HER2/neu elevated, HLA-A2' tumor targets derived from the Oregon Health Sciences University tumor bank. The chromium release assay is a standard method used for the determination of the ability of activated cytotoxic T-cells to kill their targets. Briefly, target cells are loaded with CTS, washed, and incubated with T-cells at effector to target ratios ranging from 1:1 to 1:10,000. Killing is a measure of the amount of radioactive chromium released into the culture supernatent at various times after incubation. Spleens from naive and infected animals are removed from mice 14–49 days post infection, and splenic cells collected for tetramer analysis and CTL assays. Secondary stimulation may be necessary before a CTL response is observed. T1 (HLA-A2$^+$–H-2$^d$) target cells loaded with either an individual HLA-A2-restricted HER2/neu epitope or one irrelevant epitope can be used. T1-cells are good secondary stimulators because they express large amounts of HLA-A2 and can be easily loaded with HLA-A2-restricted epitopes. Alternative methods of stimulation include incubation with Concanavalin A or through the T cell receptor using anti-CD3 antibodies. Concanavalin A is a plant mitogen that broadly stimulates T-cells. Anti-CD3 similarly stimulates T-cells my mimicking interaction with an antigen presenting cell. HLA-A2 tetramer positive T-cell clones for each individual epitope can be isolated and preserved.

EXAMPLE 9

Construction of a Heterologous Antigen HIV Vaccine

An HIV-1 vaccine was constructed using a modified version of Tn5-DICE . As shown in FIG. 6, the vaccine, Tn5-HIV1/SOB (human immunodeficiency virus 1/string of beads) carries a 6x-histidine site, the HLA-A2-restricted HTLV-1 tar epitope, and five HLA-A2-restricted HIV-1 epitopes (p $17_{77-85}$; p$24_{193-203}$; RT$_{267-277}$; gp$160_{313-322}$; and nef$_{71-80}$). Resolved in-frame insertions of Tn5-HIV1/SOB create a 109 amino acid product encoding each epitope.

The Tn5-HIV 1/SOB construct was transferred to a Nal' Salmonella recipient by conjugation, and P22 was used to make a pooled lysate, using the methods described in EXAMPLES 1 and 6. Phage lysates were used to mutagenize S. typhimurium (wild-type strain 14028s) and S. typhi (Ty21 a vaccine strain). Salmonella molecules which elicit appropriate CTL responses are selected and tested further for their ability to engender protective immune responses. Two measures of effectiveness may be considered in assessing the efficacy of these vaccines. First, are the vaccines able to elicit a protective response against cells expressing the epitopes? Second, do these vaccines elicit a protective response against a viral challenge? Variations on the methods outlined above will be used to assess the efficacy of the vaccine both in vitro and in vivo.

EXAMPLE 10

Construction of DICE-I and DICE-II Transposomes

Figure 2:
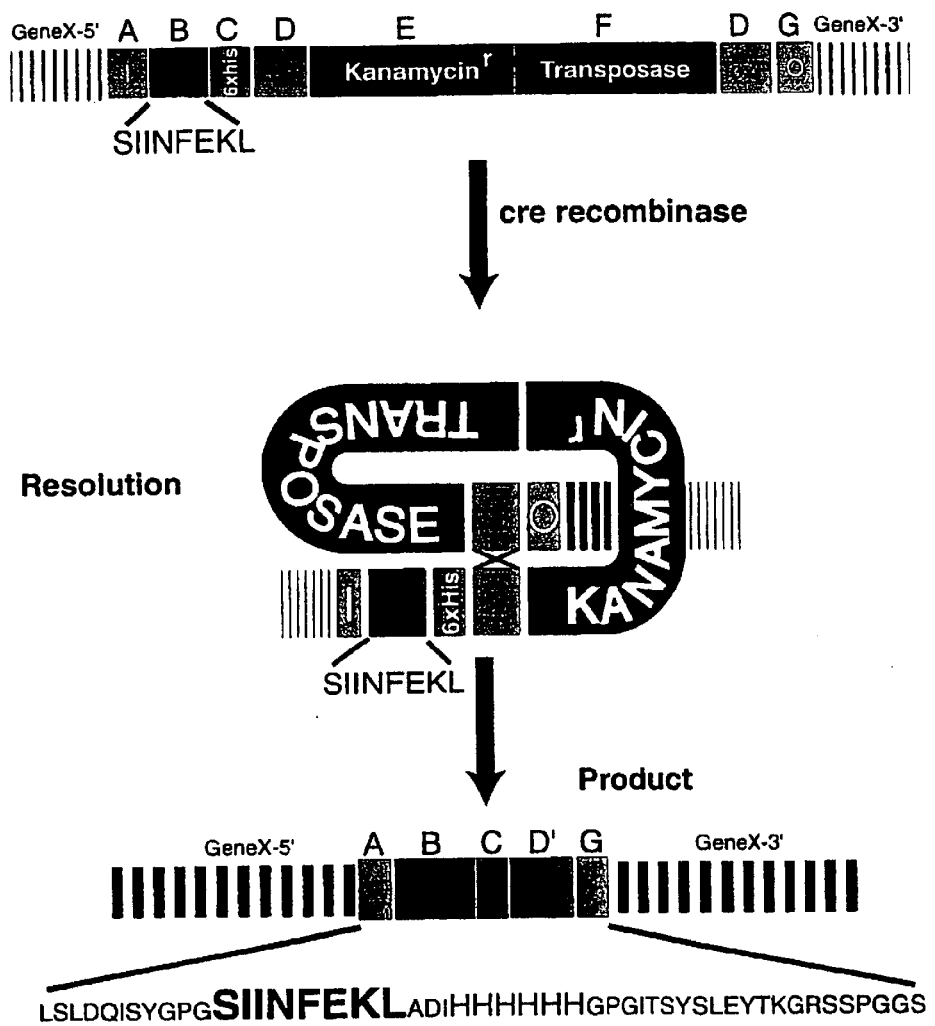
FIG. 2 is a schematic representation showing the in-frame resolution of Tn5-DICE which was used to generate the expression of fusion proteins containing the SIINFEKL epitope and a 6x-histidine tag.

The Tn5-DICE transposon shown in FIG. 2 can be engineered to accept a variety of different elements. For example, transposomes which can be used to identify Salmonella proteins (or those from a variety of infectious bacterial agents described above) which cycle into the MHC class I or class 11 (MHC, HLA) pathway can be generated. Examples of transposomes which can be used to identify Salmonella proteins which cycle into the MHC class I or class II pathway include DICE I (FIG. 7) and DICE II (FIG. 8), respectively. The original Tn5-based DICE transposon was modified in DICE-I and DICE-II by removing the transposase. Removal of transposase provides many advantages. It stabilizes the insertion, improves the efficiency of library construction because many steps in the process are eliminated, for example the mating step. Removal of the transposase also increases the range of bacteria in which transposons can be used. Incorporation of the transposome into the chromosome of the bacterium can be performed by a simple electroporation procedure. The transposomes shown in FIGS. 7 and 8 have also have excessive secondary structure remove. These secondary structures, present in Tn5-DICE, made PCR and cloning less straightforward. Unique 5' and 3' PCR primer sites have been added to facilitate inverse PCR. The I- and O-ends were changed to mosaic sequences to enable efficient transposome construction.

DICE-I contains the ovalbumin epitope SIINFEKL to identify bacterial proteins which cycle into the MHC class I pathway. However, other MHC class I epitopes can be used, for example the HTLV-1tax epitope LLFGYPVYV (SEQ ID NO: 7), as well as other epitopes known in the art.

DICE II contains an I-A$^b$ restricted T-cell epitope, ASFEAQGALANIAVDKA (SEQ ID NO 8). However, other MHC class II restricted epitopes can be used, including the anti-I-A/$^k$/Hen Egg Lysozyme (HEL$_{46-61}$) or the anti-I-A$^k$/Hen Egg Lysozyme (HEL$_{116-129}$, accession # LZCH) monoclonal antibodies.

Antigen processing of bacterial antigens is complex and cell type dependent. Host immunity to bacteria requires both CD8 and CD4 responses. In general, CD8 and CD4 represent separate arms of the immune response. CD8 cells represent the cellular immune response and CD4 cells represent the humoral (antibody) immune response. Antigens that stimulate these responses are processed differently by the host cell. Since there is more than one pathway for bacterial antigens to be processed, it makes sense that a better understanding of host immunity could be acquired by determining the accessibility of bacterial antigens within each pathway. As such, tools can be designed for use in methods of studying antigen processing within the class-II MHC pathway. Such methods allow the construction of more effective vaccines by allowing the recruitment of carrier proteins to deliver antigens to the class-II MHC pathway. The methods are performed similarly to the experiments detailed above for the class-I MHC pathway, except that MHC II nucleic acid sequence is included in the transposable element, and a MHC II specific binding agent is used in the assay.

EXAMPLE 11

Construction of Other Heterologous Antigen Vaccines

By disseminating epitopes throughout the genome of Salmonella, potent vaccines can be constructed by identification and use of carrier proteins that elicit protective immune responses. Salmonella causes a disseminated infection in several different tissues. The transposable elements of the present invention can be used to identify genes expressed in different tissues, and vaccines can be constructed which tailor the immune response by using tissue-specific carrier proteins as carriers.

EXAMPLE 12

Alternate Transposable Elements

Fluorescent Protein Insertions.

Variants of the Tn5-DICE transposon and the DICE-I and DICE-II transposomes can be constructed to carry one or more genes that encode fluorescent proteins. In -frame insertions of this transposon into a gene will generate a fusion protein that carries an enhanced fluorescent protein, for example GFP (accession U55761), and red fluorescent protein (accession U70496). As used herein, GFP refers to both the wild-type protein, and spectrally shifted mutants thereof, for example as described in Tsien, 1998, *Ann. Rev. Biochem.* 67:509 and in U.S. Pat. Nos. 5,777,079 and 5,625,048 to Tsien and Heim, herein incorporated by reference. Asparyginyl endopeptidase cleavage sites enable the fluorescent protein to be cleaved from the fusion product eliminating conformational distortions and allow the protein to fluoresce. The GFP gene would be placed within the same location as the I-A$^b$ restricted T-cell epitope, ASFEAQ-GALANIAVDKA contained in DICE-II. The GFP or RFP genes would be modified to remove termination signals to allow transcriptional and translational readthrough after insertion and resolution.

Addition of one or more fluorophores may allow the host bacterial range of the system to be greatly expanded, because it would enable the identification in vivo of expressed genes by FACS analysis of tissue homogenates as described in EXAMPLE 2. Protein products identified by this transposon/transposome variant can be use to identify efficacious bacterial vaccine antigens in previously genetically intractable microorganisms that are pathogenic to humans and animals. These transposon/transposome variants can be used to identify secreted bacterial antigens by direct sorting of infected fluorescent host cells.

Customized Effector Proteins.

Variants of the Tn5-transposon and the DICE-I and DICE-II transposomes can be generated to engineer bacterial carrier vaccines to deliver customized host effector molecules. For instance, by delivering a fragment or an entire host signaling factor into the host cell after uptake of the vaccine, the immune response could thus be skewed to a more efficacious response. Candidate signaling molecules include, but are not limited those in the Jak/Stat pathway.

Vaccines having the ability to appropriately bias the immune response avoid many of the deleterious side effects associated with traditional vaccines. In addition, vaccines can be constructed to enable the treatment of acute pathogenic infections. The response to these types of vaccines would be quick, strong, specific, and transient These types of vaccines are desired by the armed forces as a means of dealing with bio-warfare exposure.

Multivalent Vaccines.

A variant of the vaccines described in the above examples that delivers epitopes from more than one organism can be generated. *Salmonella* can be used to construct multivalent vaccines since it is capable of carrying large amounts of accessory DNA encoding vaccine antigens. The strength of the DICE system lies in its ability to identify appropriate carrier proteins for combinations of epitopes.

Many pathogenic infections potentiate the growth of additional microorganisms that are different from the primary infection. Such vaccines can be used as a "one shot" method of protection.

Host Receptor Delivey.

Variants of the transposon/transposases that deliver a molecule that will localize to the surface of the host cell can be generated. Such constructs have at least two potential uses. First, they would allow secreted bacterial proteins to be identified after infection by looking for the presence of the secreted protein on the surface of the host cell. Second, these variants could deliver chimeric signaling molecules (molecules which associate to the cell surface and initiate internal signaling in response to an external signal). For example, delivering the vaccine then subsequently activating the response after treatment with a drug. This would allow antigen to be loaded into an APC and thus augment the immune response.

Alpha-Omega Complementation.

Variants of the transposon/transposome that encode the α-fragment from β-galactosidase can be generated. Many bacteria are not amenable to the analysis of secreted proteins because tools are not available that allow the identification of secreted genes by their MHC-restriction. This transposon/transposome variant will enable the bacteria to secrete fusion proteins that contain the α-fragment from β-galactosidase. Secreted proteins can be detected because the host cell (or a transgenic host animal) expresses the omega fragment from β-galactosidase. When the secreted α-fragment and the host omega fragment come into contact to form a functional β-galactosidase complex, various enzyme substrates can be used to visualize the interaction. For instance, the substrate $C_{12}$FDG (Molecular Probes, #1-2904) becomes fluorescent when cleaved by functional β-galactosidase. Alternatively, the commonly used substrate X-gal could be used to visualize active β-galactosidase within a cell. With system, pathogenesis can be studied in whole animals by looking for the presence of fluorescent bacteria in different host tissues. In addition, tissue-specific secretion of bacterial proteins could be determined and thus enable optimized carrier vaccines that secrete antigen in appropriate host compartments.

EXAMPLE 13

Other Uses of Transposable Elements

The transposable elements of the present invention can also be used to modify vaccine carrier strains of *Salmonella* to augment or skew the immune response to the carried antigen by delivering eukaryotic effector proteins such as Jak2 or Tyk2 as CAP fusions. Mutants generated by the transposable elements can be used to identify tissue-specific *Salmonella* CAPs, potentially useful proteins for regulating the timing of the immune response to carried antigens and thus generate immune responses more amenable to the lifecycle of different pathogens. For instance, JAK2 (a host kinase) initiates a signaling cascade that ultimately results in the upregulation of cytokines that enhance the cell-mediated immune response. In principle, the transposon could be engineered to deliver JAK2 (or a portion of JAK2) and bias the immune response to one that is predominately cell mediated.

EXAMPLE 14

Functional Genomics

Genomic sequencing of pathogens provides valuable insights into the lifestyle of a variety of different organisms. Data from these projects however reveal that as much as 40% of genes have no known function. Therefore, methods are needed to rapidly assign function to genes identified by genomic projects. Since the transposable elements of the present invention can be constructed to carry an affinity tag such as a 6× histidine site, immunolocalization studies can provide valuable insight into the function of genes identified by genomic sequencing projects.

EXAMPLE 15

Construction or Customized Effector Molecules

Specific immune responses are generated as a consequence of a cascade of signal transduction events. DICE identifies proteins that have access to the cytoplasm of the host cell. DICE technology can be used to construct customized effector molecules whose function would be to skew the immune response and generate a bacterial carrier vaccine appropriate to clearance of the pathogen.

EXAMPLE 16

Identification of Diagnostic Proteins

The emergence of new, more virulent bacterial strains, coupled with the threat of biological terrorism, emphasizes the need for targets that will allow the rapid and precise identification of different pathogens. DICE enable the identification of species-specific genes utilized by the pathogen during the course of infection.

EXAMPLE 17

Transfer of DNA into Cells

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, 1973, *Virology* 52:466) or strontium phosphate (Brash et al., 1987, Mol. Cell Biol. 7;2013), electroporation (Neumann et al., 1982, *EMBO J.* 1:841), lipofection (Felgner et al., 1987, Proc. Nail. Acad Sci USA 84:7413), DEAE dextran (McCuthan et al., 1968, *J. Natl. Cancer Inst.* 41:351), microinjection (Mueller et al., 1978, *Cell* 15:579), protoplast fusion (Schafner, 1980, Proc. Nail. Acad. Sci. USA 77:2163–7), or pellet guns (Klein et al., 1987, *Nature* 327:70). Alternatively, the cDNA can be introduced by infection with virus vectors. Systems are developed that use, for example, retroviruses (Bernstein et al., 1985, *Gen. Engrg.* 7:235), adenoviruses (Ahmad et al., 1986, *J. Virol.* 57:267), or Herpes virus (Spaete et al., 1982, *Cell* 30:295).

EXAMPLE 18

Sequence Variants of Transposable Elements

Having presented a format of the transposable elements of the present invention, and the sequence of DICE-I and DICE-II, this invention now also facilitates the creation of DNA molecules, and thereby proteins, which are derived from those disclosed but which vary in their precise nucleotide or amino acid sequence from those disclosed. Such variants may be obtained through a combination of standard molecular biology laboratory techniques and the nucleotide sequence information disclosed by this invention.

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

Variant DNA molecules include those created by standard DNA mutagenesis techniques, for example, M13 primer mutagenesis. Details of these techniques are provided in Sambrook et al. (In: *Molecular Cloning: A Laboratory Manual*, Cold Spring Harbor, N.Y., 1989, Ch. 15, herein incorporated by reference). By the use of such techniques, variants may be created which differ in minor ways from those disclosed. DNA molecules and nucleotide sequences which are derivatives of those specifically disclosed herein and which differ from those disclosed by the deletion, addition or substitution of nucleotides while still encoding a protein which possesses the functional characteristics of the proteins which are comprehended by this invention.

Also within the scope of this invention are small DNA molecules which are derived from the disclosed DNA molecules. Such small DNA molecules include oligonucleotides suitable for use as hybridization probes or PCR primers. As such, these small DNA molecules will include at least a segment of the transposable element DNA molecules and, for the purposes of PCR, will include at least 20–50 consecutive nucleotides of the transposable element nucleic acid sequences. DNA molecules and nucleotide sequences which are derived from the disclosed DNA molecules as described above may also be defined as DNA sequences which hybridize under stringent conditions to the DNA sequences disclosed, or fragments thereof.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. (In: *Molecular Cloning: A Laboratory Manual*, Cold Spring Harbor, N.Y., 1989 ch. 9 and 11), herein incorporated by reference. By way of illustration only, a hybridization experiment may be performed by hybridization of a DNA molecule (for example, a deviation of the transposable element) to a target DNA molecule (for example, a transposable element DNA) which has been electrophoresed in an agarose gel and transferred to a nitrocellulose membrane by Southern blotting (Southern, *J. Mol. Biol.* 98:503, 1975), a technique well known in the art and described in Sambrook et al. (*Molecular Cloning: A Laboratory Manual*, Cold Spring Harbor, N.Y., 1989).

Hybridization with a target probe labeled with [$^{32}P$]-dCTP is generally carried out in a solution of high ionic strength such as 6×SSC at a temperature that is 20–25° C. below the melting temperature, $T_m$, described below. For such Southern hybridization experiments where the target DNA molecule on the Southern blot contains 10 ng of DNA or more, hybridization is typically carried out for 6–8 hours using 1–2 ng/ml radiolabeled probe (of specific activity equal to $10^9$ CPM/µg or greater). Following hybridization, the nitrocellulose filter is washed to remove background hybridization. The washing conditions should be as stringent as possible to remove background hybridization but to retain a specific hybridization signal. The term $T_m$ represents the temperature above which, under the prevailing ionic conditions, the radiolabeled probe molecule will not hybridize to its target DNA molecule. The $T_m$ of such a hybrid molecule may be estimated from the following equation (Bolton and McCarthy, *Proc. Natl. Acad. Sci. USA* 48:1390, 1962): $T_m = 81.5°$ C.$-16.6(\log_{10}[Na^+])+0.41(\%$ G+C$)-0.63(\%$ formamide$)*(600/1)$; where I=the length of the hybrid in base pairs.

This equation is valid for concentrations of $Na^+$ in the range of 0.01 M to 0.4 M, and it is less accurate for calculations of $T_m$ in solutions of higher [Na$^+$]. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al. (*Molecular Cloning: A Laboratory Manual*, Cold Spring Harbor, N.Y., 1989).

Thus, by way of example, for a 150 base pair DNA probe derived from a transposable element nucleic acid sequence (with a hypothetical % GC=45%), a calculation of hybridization conditions required to give particular stringencies may be made as follows: For this example, it is assumed that the filter will be washed in 0.3×SSC solution following hybridization, thereby: [Na$^+$]=0.045 M; % GC=45%; Formamide concentration=0; l=150 base pairs; $T_m$=81.5−16.6 (log$_{10}$[Na$^+$])+(0.41×45)−(600/150); and so $T_m$=74.4° C.

The $T_m$ of double-stranded DNA decreases by 1–1.5° C. with every 1% decrease in homology (Bonner et al., *J. Mol. Biol.* 81:123, 1973). Therefore, for this given example, washing the filter in 0.3×SSC at 59.464.4° C. will produce a stringency of hybridization equivalent to 90%; that is, DNA molecules with more than 10% sequence variation relative to the target transposable element DNA will not hybridize. Alternatively, washing the hybridized filter in 0.3×SSC at a temperature of 65.4–68.4° C. will yield a hybridization stringency of 94%; that is, DNA molecules with more than 6% sequence variation relative to the target transposable element DNA molecule will not hybridize. The above example is given entirely by way of theoretical illustration. One skilled in the art will appreciate that other hybridization techniques may be utilized and that variations in experimental conditions will necessitate alternative calculations for stringency.

In particular embodiments of the present invention, stringent conditions may be defined as those under which DNA molecules with more than 25%, 15%, 10%, 6% or 2% sequence variation (also termed "mismatch") will not hybridize.

The degeneracy of the genetic code further widens the scope of the present invention as it enables major variations in the nucleotide sequence of a DNA molecule while maintaining the amino acid sequence of the encoded protein. For example, the C-terminal amino acid residue of the transposable element Tn5-DICE is alanine. This is encoded in the Tn5-DICE DNA by the nucleotide codon triplet GCG. Because of the degeneracy of the genetic code, other nucleotide codon triplets, could encode the C-terminal amino acid residue (e.g. GCT and GCC), as they also code for alanine. Thus, the nucleotide sequence of the Tn5-DICE cDNA could be changed at this position to any of these three codons without affecting the amino acid composition of the encoded protein or the characteristics of the protein. Based upon the degeneracy of the genetic code, variant DNA molecules may be derived from the cDNA molecules disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein also comprehended by this invention.

The invention also includes DNA sequences that are substantially identical to any of the DNA sequences disclosed herein, where substantially identical means a sequence that has identical nucleotides in at least 70%, 75%, 80%, 85%, 90%, 95%, 98% or 99% of the aligned sequences.

One skilled in the art will recognize that the DNA mutagenesis techniques described above may be used not only to produce variant DNA molecules, but will also facilitate the production of proteins which differ in certain structural aspects from the transposable elements, yet which proteins are clearly derivative of this protein and which maintain the essential characteristics of the proteins of the transposable elements. Newly derived proteins may also be selected in order to obtain variations on the characteristic of the transposable element protein, as will be more fully described below. Such derivatives include those with variations in amino acid sequence including minor deletions, additions and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

Amino acid substitutions are typically of single residues; insertions usually will be on the order of about from 1 to 10 amino acid residues; and deletions will range about from 1 to 30 residues. Deletions or insertions may be made in adjacent pairs, i.e., a deletion of 2 residues or insertion of 2 residues. Substitutions, deletions, insertions or any combination thereof may be combined to arrive at a final construct. Obviously, the mutations that are made in the DNA encoding the protein must not place the sequence out of reading frame and ideally will not create complementary regions that could produce secondary mRNA structure.

Substitutional variants are those in which at least one residue in the amino acid sequence has been removed and a different residue inserted in its place. Such substitutions generally are made conservatively, as defined above.

Substantial changes in function or immunological identity are made by selecting substitutions that are less conservative than those defined above, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives of the transposable elements by assays in which the ability of the elements to transpose are assessed.

EXAMPLE 19

Pharmaceutical Compositions and Modes of Administration

Various delivery systems for administering the transposable elements of the present invention are known, and include e.g., encapsulation in liposomes, microparticles, microcapsules, expression by recombinant cells, receptor-mediated endocytosis (see Wu and Wu, *J. Biol. Chem.* 1987, 262:4429–32), and construction of a therapeutic nucleic acid as part of a retroviral or other vector. Methods of introduction include, but are not limited to, intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, the pharmaceutical compositions may be introduced into the central nervous system by any suitable route, including intraventricular and intrathecal injection; intraventricular injection may be facilitated by an intraventricular catheter, for example, attached to a reservoir, such as an Ommaya reservoir.

In one embodiment, it may be desirable to administer the pharmaceutical compositions of the invention locally to the area in need of treatment, for example, by local infusion during surgery, topical application, e.g., in conjunction with a wound dressing after surgery, by injection, through a catheter, by a suppository ran implant, such as a porous, non-porous, or gelatinous material, including membranes, such as silastic membranes, or fibers. In one embodiment, administration can be by direct injection at the site (or former site) of a malignant tumor or neoplastic or pre-neoplastic tissue.

The use of liposomes as a delivery vehicle is one delivery method of interest. The liposomes fuse with the target site and deliver the contents of the lumen intracellularly. The liposomes are maintained in contact with the target cells for a sufficient time for fusion to occur, using various means to maintain contact, such as isolation and binding agents. Liposomes may be prepared with purified proteins or peptides that mediate fusion of membranes, such as Sendai virus or influenza virus. The lipids may be any useful combination of known liposome forming lipids, including cationic lipids, such as phosphatidylcholine. Other potential lipids include neutral lipids, such as cholesterol, phosphatidyl serine, phosphatidyl glycerol, and the like. For preparing the liposomes, the procedure described by Kato et al. (*J Biol. Chem.* 1991, 266:3361) may be used.

The present invention also provides pharmaceutical compositions which include a therapeutically effective amount of the transposable element, alone or with a pharmaceutically acceptable carrier. In one example, homogeneous compositions of transposable element therapeutic molecules includes compositions that are comprised of at least 90°% of the peptide, variant, analog, derivative or mimetic in the composition.

Delivery System

Such carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate.

The amount of the inducing agent and disrupting agent that will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. Effective doses may be extrapolated from dose-response curves derived from in vitro or animal model test systems.

The invention also provides a pharmaceutical pack or kit comprising one or more containers filled with one or more often ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration. Instructions for use of the composition can also be included.

The pharmaceutical compositions or methods of treatment may be administered in combination with other therapeutic treatments, such as other antineoplastic or antitumorigenic therapies.

Administration of Nucleic Acid Molecules

In an embodiment in which a transposable element nucleic acid is employed for gene delivery or therapy, the analog is delivered intracellularly (e.g., by expression from a nucleic acid vector or by receptor-mediated mechanisms). In a specific embodiment where the therapeutic molecule is a nucleic acid or antisense molecule, administration may be achieved by an appropriate nucleic acid expression vector which is administered so that it becomes intracellular, e.g., by use of a retroviral vector (see U.S. Pat. No. 4,980,286), or by direct injection, or by use of microparticle bombardment (e.g., a g ene gun; Biolistic, Dupont), or coating with lipids or cell-surface receptors or transfecting agents, or by administering it in linkage to a homeobox-like peptide which is known to enter the nucleus (see e.g., Joliot et al., *Proc. Natl. Acad Sci. USA* 1991, 88:1864.8). Alternatively, the nucleic acid can be introduced intracellularly and incorporated within host cell DNA for expression, by homologous recombination.

The vector pcDNA, is an example of a method of introducing the foreign cDNA into a cell under the control of a strong viral promoter (CMV) to drive the expression. However, other vectors can be used. Other retroviral vectors (such as pRETRO-ON, Clontech), also use this promoter but have the advantages of entering cells without any transfection aid, integrating into the genome of target cells only when the target cell is dividing (as cancer cells do, especially during first remissions after chemotherapy) and they are regulated. It is also possible to turn on the expression of the transposable element nucleic acid by administering tetracycline when these plasmids are used. Hence these plasmids can be allowed to transfect the cells, then administer a course of tetracycline with a course of chemotherapy to achieve better cytotoxicity.

Other plasmid vectors, such as pMAM-neo (Clontech) or pMSG (Amersham Pharmacia Biotech, Piscataway, N.J.) use the MMTV-LTR promoter (which can be regulated with steroids) or the SV10 late promoter (pSVL, Amersham Pharmacia Biotech, Piscataway, N.J.) or metallothionein-responsive promoter (pBPV, Amersham Pharmacia Biotech) and other viral vectors, including retroviruses. Examples of other viral vectors include adenovirus, AAV (adeno-associated virus), recombinant HSV, poxviruses (vaccinia) and recombinant lentivirus (such as HIV). All these vectors achieve the basic goal of delivering into the target cell the cDNA sequence and control elements needed for transcription. The present invention includes all forms of nucleic acid delivery, including synthetic oligos, naked DNA, plasmid and viral, integrated into the genome or not.

Having illustrated and described the principles of constructing and using transposable elements, it should be apparent to one skilled in the art that the invention can be modified in arrangement and detail without departing from such principles. In view of the many possible embodiments to which the principles of our invention may be applied, it should be recognized that the illustrated embodiments are only examples of the invention and should not be taken as a limitation on the scope of the invention. Rather, the scope of the invention is in accord with the following claims. We therefore claim as our invention all that comes within the scope and spirit of these claims.

---

We claim:

1. A method for identifying a protein secreted by an intracellular pathogen and having access to an MHC class I pathway of a eukaryotic cell infected with the intracellular pathogen, comprising:

(i) transfecting intracellular pathogen with a transposable element, wherein the transposable element has a 3' and a 5' end and comprises a 5' recombining site 5' of a nucleic acid sequence encoding a selectable marker, a 3' recombining site 3' of the nucleic acid sequence encoding a selectable marker, a nucleic acid sequence encoding an MHC class I epitope 5' to the 5' recombining site or 3' to the 3' recombining site, and an insertion end comprising an inverted repeat sequence sufficient for integration of the transposable element at the 5' and the 3' end of the transposable element, and wherein the transfection results in the integration of the transposable element in a nucleic acid sequence of the intracellular pathogen;

(ii) transforming the intracellular pathogen with a vector comprising a transposase;

(iii) contacting a eukaryotic cell that can internalize the intracellular pathogen with the pathogen transfected with the transposable element, wherein an MHC class I haplotype of the eukaryotic cell is matched to the MHC I epitope;

(iv) contacting the eukaryotic cell with a labeled antibody that recognizes the MHC class I epitope, thereby generating a labeled eukaryotic cell;

(v) identifying the labeled eukaryotic cell;

(vi) lysing the labeled eukaryotic cell to externalize the intracellular pathogen;

(vii) growing the externalized intracellular pathogen to produce a population of intracellular pathogen; and (viii) identifying the nucleic acid sequence of the intracellular pathogen that has the integrated transposable element, wherein the nucleic acid sequence encodes the secreted protein having access to an MHC class I pathway of eukaryotic cell infected with the intracellular pathogen.

2. The method of claim 1, wherein the eukaryotic cell is a cell of the immune system.

3. The method of claim 2, wherein the cell of the immune system is a macrophage.

4. The method of claim 1, wherein the identification of the labeled eukaryotic cell is by fluorescence activated cell sorting.

5. The method of claim 1, wherein the intracellular pathogen is a bacterial cell.

6. The method of claim 1, wherein the pathogen is *Salmonella, Mycobacterium tuberculosis, Plasmodium*, or *Listeria monocytogenes*.

7. The method of claim 1, wherein the 5' recombining site or the 3' recombining site is a loxP recombining site, a fit recombining site, a TN3 recombining site, a mariner recombining site, or a gamma/delta recombining site.

8. The method of claim 1, wherein the 5' recombining site or the 3' recombining site is a loxP recombining site.

9. The method of claim 8, wherein the loxP sequence comprises the sequence shown in SEQ ID NO: 11.

10. The method of claim 1, wherein the MHC class I epitope is SIINFEKL (SEQ ID NO: 6) and the MHC class I haplotype of the eukaryotic cell is H-2 Kb.

11. The method of claim 1, wherein the selectable marker is a nucleic acid encoding antibiotic resistance.

12. The method of claim 11, wherein the antibiotic resistance is ampicillin, kanamycin, zeomycin, hygromycin, tetracycline, puromycin or bleomycin resistance.

13. The method of claim 1, wherein the selectable marker is detected by spectrophotometric properties.

14. The method of claim 1, wherein the selectable marker is beta-galactosidase or green fluorescent protein.

15. The method of claim 1, wherein the insertion end at the 5' end of the transposable element is SEQ ID NO: 4 or SEQ ID NO: 5.

16. The method of claim 15, wherein the insertion end at the 5' end of the transposable element comprises the sequence shown in SEQ ID NO: 5.

17. The method of claim 1, wherein the insertion end at the 3' end of the transposable element is SEQ ID NO: 3 or SEQ ID NO: 4.

18. The method of claim 17, wherein the insertion end at the 3' end of the transposable element comprises the sequence shown in SEQ ID NO: 3.

19. The method of claim 1, wherein the transposable element further comprises a nucleic acid sequence encoding a transposase.

20. The method of claim 19, wherein the transposase is a Cre transposase.

21. The method of claim 1, wherein the transposable element further comprises an affinity tag.

22. The method of claim 21, wherein the affinity tag is 6× histidine, S-tag, glutathione-S-transferase, or streptavidin.

23. The method of claim 22, wherein the affinity tag is 6× histidine.

24. The method of claim 21, wherein the nucleic acid sequence encoding an affinity tag is 5' of the 5' recombining site.

25. The method of claim 21, wherein the nucleic acid sequence encoding an affinity tag is 3' of the 3' recombining site.

26. The method of claim 1, wherein the MHC class I epitope is LLFGYPVYV (SEQ ID NO: 7) and the MHC class I haplotype of the eukaryotic cell is HLA-A2.

27. A method for identifying a protein secreted by an intracellular pathogen and having access to an MHC class I pathway of a eukaryotic cell infected with the intracellular pathogen, comprising:

(i) transfecting an intracellular pathogen expressing a tranposase with a transposable element wherein the transposable element has a 3' and a 5' end and comprises a 5' recombining site 5' of a nucleic acid sequence encoding a selectable marker, a 3' recombining site 3' of the nucleic acid sequence encoding a selectable marker, a nucleic acid sequence encoding an MHC class I epitope 5' to the 5' recombining site or 3' to the 3' recombining site, and an insertion end comprising an inverted repeat sequence sufficient for integration of the transposable element at the 5' and the 3' end of the transposable element, and wherein the transfection results in the integration of the transposable element in a nucleic acid sequence of the intracellular pathogen;

(ii) contacting a eukaryotic cell that can internalize the intracellular pathogen with the pathogen transfected with the transposable element, wherein an MHC class I haplotype of the eukaryotic cell is matched to the MHC I epitope;

(iii) contacting the eukaryotic cell with a labeled antibody that recognizes the MHC class I epitope, thereby generating a labeled eukaryotic cell;

(iv) identifying the labeled eukaryotic cell;

(v) lysing the labeled eukaryotic cell to externalize the intracellular pathogen;

(vi) growing the externalized pathogen to produce a population of intracellular pathogen; and (vii) identifying the nucleic acid sequence of the intracellular pathogen that has the integrated transposable element, wherein the nucleic acid sequence encodes the secreted protein having access to an MHC class I pathway of a eukaryotic cell infected with the intracellular pathogen.

28. The method of claim 27, wherein the 5' recombining site or the 3' recombining site is a loxP recombining site, a fit recombining site, a TN3 recombining site, a mariner recombining site, or a gamma/delta recombining site.

29. The method of claim 28, wherein the 5' recombining site or the 3' recombining site is a loxP recombining site.

30. The method of claim 29, wherein the loxP sequence comprises the sequence shown in SEQ ID NO: 11.

31. The method of claim 27, wherein the MHC class I epitope is SIINFEKL (SEQ ID NO: 6) and the MHC class I haplotype of the eukaryotic cell is H-2 Kb.

32. The method of claim 27, wherein the selectable marker is a nucleic acid encoding antibiotic resistance.

33. The method of claim 27, wherein the selectable marker is detected by spectrophotometric properties.

34. The method of claim 27, wherein the insertion end at the 5' end of the transposable element is SEQ ID NO: 4 or SEQ ID NO: 5.

35. The method of claim 27, wherein the insertion end at the 3' end of the transposable element is SEQ ID NO; 3 or SEQ ID NO: 4.

36. The method of claim 27, wherein the transposable element further comprises an affinity tag.

37. The method of claim 36, wherein the affinity tag is 6× histidine, S-tag, glutathione-S-transferase, or streptavidin.

38. The method of claim 36, wherein the nucleic acid sequence encoding an affinity tag is 5' of the 5' recombining site.

39. The method of claim 36, wherein the nucleic acid sequence encoding an affinity tag is 3' of the 3' recombining site.

40. The method of claim 27, wherein the MHC class I epitope is LLFGYPVYV (SEQ ID NO: 7) and the MHC class I haplotype of the eukaryotic cell is HLA-A2.

41. A method for identifying a protein secreted by an intracellular pathogen and having access to an MHC class I pathway of a eukaryotic cell infected with the intracellular pathogen, wherein the intracellular pathogen is a bacterial cell, comprising:
   (i) transfecting an intracellular pathogen with a transposable element, wherein the transposable element has a 3' and a 5' end and comprises a 5' recombining site 5' of a nucleic acid sequence encoding a selectable marker, a 3' recombining site 3' of the nucleic acid sequence encoding a selectable marker, a nucleic acid sequence encoding an MHC class I epitope 5' to the 5' recombining site or 3' to the 3' recombining site, an insertion end comprising an inverted repeat sequence sufficient for integration of the transposable element at the 5' and the 3' end of the transposable element, and a transposase, and wherein the transfection results in the integration of the transposable element in a nucleic acid sequence of the intracellular pathogen;
   (ii) contacting a eukaryotic cell that can internalize the intracellular pathogen with the pathogen transfected with the transposable element, wherein an MHC class I haplotype of the eukaryotic cell is matched to the MHC I epitope;
   (iii) contacting the eukaryotic cell with a labeled antibody that recognizes the MHC class I epitope, thereby generating a labeled eukaryotic cell;
   (iv) identifying the labeled eukaryotic cell;
   (v) lysing the labeled eukaryotic cell to externalize the intracellular pathogen;
   (vi) growing the externalized bacterial cell to produce a population of intracellular pathogen; and
   (vii) identifying the nucleic acid sequence of the intracellular pathogen that has the integrated transposable element, wherein the nucleic acid sequence encodes the secreted protein having access to an MHC class I pathway of a eukaryotic cell infected with the intracellular pathogen.

42. The method of claim 41, wherein the 5' recombining site or the 3' recombining site is a loxP recombining site, a flt recombining site, a TN3 recombining site, a mariner recombining site, or a gamma/delta recombining site.

43. The method of claim 42, wherein the 5' recombining site or the 3' recombining site is a loxP recombining site.

44. The method of claim 43, wherein the loxP sequence comprises the sequence shown in SEQ ID NO: 11.

45. The method of claim 41, wherein the MHC I epitope is SIINFEKL (SEQ ID NO: 6) and the MHC class I haplotype of the eukaryotic cell is H-2 Kb.

46. The method of claim 41, wherein the selectable marker is a nucleic acid encoding antibiotic resistance.

47. The method of claim 41, wherein the selectable marker is detected by spectrophotometric properties.

48. The method of claim 41, wherein the insertion end at the 5' end of the transposable element is SEQ ID NO: 4 or SEQ ID NO: 5.

49. The method of claim 41, wherein the insertion end at the 3' end of the transposable element is SEQ ID NO: 3 or SEQ ID NO: 4.

50. The method of claim 46, wherein the transposable element further comprises an affinity tag.

51. The method of claim 50, wherein the affinity tag is 6× histidine, S-tag, glutathione-S-transferase, or streptavidin.

52. The method of claim 50, wherein the nucleic acid sequence encoding an affinity tag is 5' of the 5' recombining site.

53. The method of claim 50, wherein the nucleic acid sequence encoding an affinity tag is 3' of the 3' recombining site.

54. The method of claim 41, wherein the MHC class I epitope is LLFGYPVYV (SEQ ID NO: 7) and the MHC class I haplotype of the eukaryotic cell is HLA-A2.

* * * * *

UNITED STATES PATENT AND TRADEMARK OFFICE
CERTIFICATE OF CORRECTION

PATENT NO. : 6,846,622 B1
APPLICATION NO. : 09/979338
DATED : January 25, 2005
INVENTOR(S) : Heffron et al.

Figure 3A:
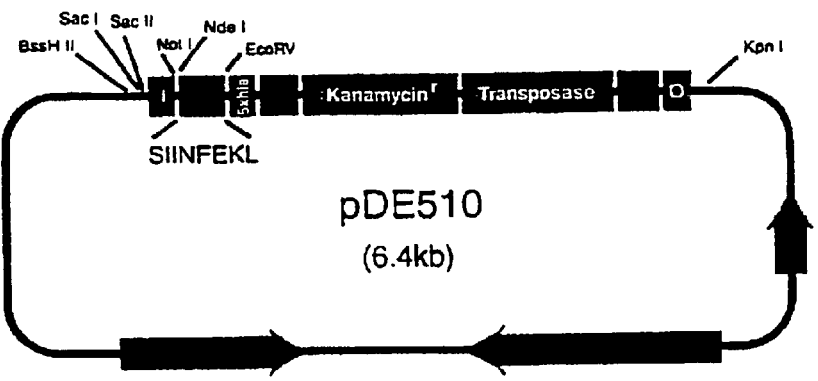
FIG. 3 is a schematic representation of some plasmids used for DICE analysis. A. Pasmid carrying a Tn5-DICE resolvable transposon; B. Arabinose inducible cre recombinase plasmid pBAD33cre.
Figure 3B:
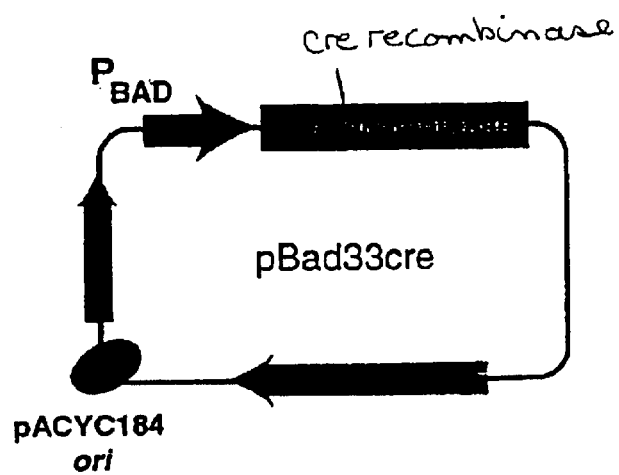

It is certified that error appears in the above-identified patent and that said Letters Patent is hereby corrected as shown below:

In the Drawings:

Fig. 3A, "5xhla" should be --6xhis--.

Figure 9:
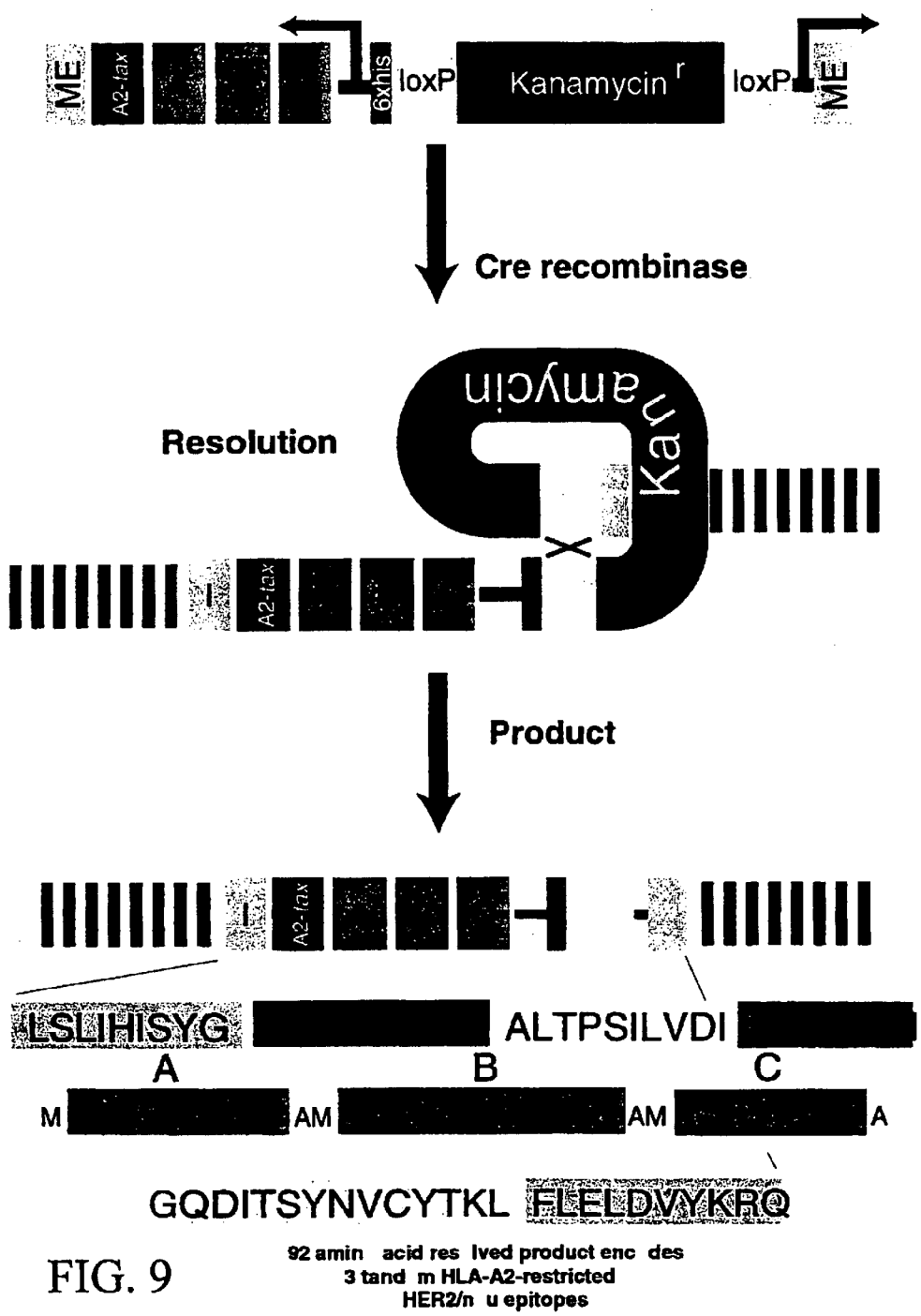
FIG. 9 is a schematic representation of a *Salmonella*-HER2/neu epitope carrier vaccine.

Fig. 9, "res lvd" should be --resolved--; "enc des" should be --encodes--; "tand m" should be --tandem--; and "HER2/n u" should be --HER2/neu--.

Figure 10:
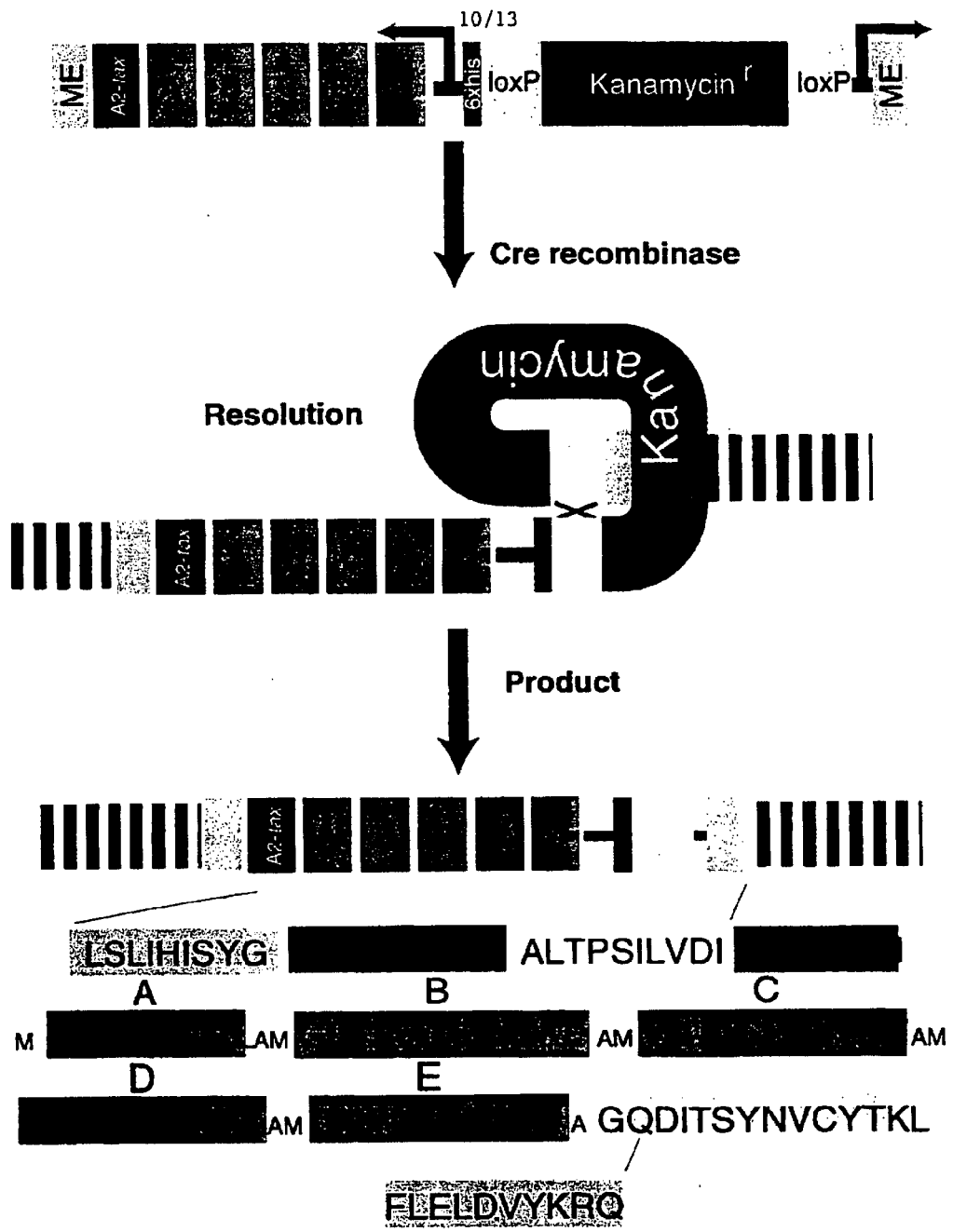
FIG. 10 is a schematic representation of a *Salmonella*-HIV epitope carrier vaccine.

Fig. 10, "epit pes" should be --epitopes--.

In the Specification:

Column 1, line 59, "expressi n" should be --expression--.

Column 2, line 45, "element" shoul be --element.--.

Column 3, line 43, "Tn5-DICE" should be --Tn5-DICE (SEQ ID NO: 26)--.

Column 3, lines 44-45, "SIINFEKL epitope and a 6×-histidine tag" should be --SIINFEKL (SEQ ID NO: 6) epitope and a 6×-histidine tag (SEQ ID NO: 13)--.

Column 3, line 47, "Pasmid carrying" should be --Plasmid carrying--.

Column 3, line 54, "mutant" should be --mutant.--.

Column 3, line 62, "construct" should be --(SEQ ID NO: 27) construct--.

Column 3, line 64, "construct" should be --construct (SEQ ID NO: 28)--.

Column 3, line 66, "transposome," should be --transposome (SEQ ID NO: 29),--

Column 4, line 2, "transposome," should be --transposome (SEQ ID NO: 30),--

Column 4, line 5, "vaccine." should be --vaccine (SEQ ID NO: 31).--.

Column 4, line 7, "vaccine." should be --vaccine (SEQ ID NO: 32).--.

Column 4, line 8, "sequences." should be --sequences (SEQ ID NOS: 8-10).--.

Column 4, line 9, "Sequences." should be --Sequences (SEQ ID NOS: 22 and 23).--.

Column 4, line 10, "Sequences." should be --Sequences (SEQ ID NOS: 24 and 25).--.

UNITED STATES PATENT AND TRADEMARK OFFICE
CERTIFICATE OF CORRECTION

| | |
|---|---|
| PATENT NO. | : 6,846,622 B1 |
| APPLICATION NO. | : 09/979338 |
| DATED | : January 25, 2005 |
| INVENTOR(S) | : Heffron et al. |

It is certified that error appears in the above-identified patent and that said Letters Patent is hereby corrected as shown below:

Column 4, line 24, "SEQ ID NO 2is" should be --SEQ ID NO 2 is--.

Column 4, line 29, "an 1 end" should be --an I end--.

Column 4, line 33, "SEQ ID NO 8 is the ASFEAQGALANIAVDKA epitope." should be deleted, and --SEQ ID NOS: 8-10 show Tn5 Mosaic end amino acid sequences.-- should be added.

Column 4, line 34, "SEQ ID NO 9" should be --SEQ ID NO: 11--.

Column 4, line 36, "SEQ ID NO 10 is the-sequence of the 6×histidine, shown as position 82-100 of Fig. 12." should be --SEQ ID NOS: 12 and 13 are the nucleic acid and amino acid sequences, respectively, of the 6X histidine, shown as position 82-100 of Fig. 12--.

Column 4, line 39, "SEQ ID NO 11" should be --SEQ ID NO: 14--, and "shown a position" should be -- shown as position--.

Column 4, line 41, "SEQ ID NO 12" should be --SEQ ID NO: 15--.

Column 4, line 43, "SEQ ID NO 13" should be --SEQ ID NO: 16--.

Column 4, line 45, "SEQ ID NO 14" should be --SEQ ID NO: 17--.

Column 4, line 48, "SEQ ID NO 15" should be --SEQ ID NO: 18--.

Column 4, line 52, the following 12 paragraphs should be added:
  --SEQ ID NOS: 19 and 20 show a nucleic acid and an amino acid sequence of an I-$A^b$ restricted T-cell epitope.
  SEQ ID NO: 21 is a nucleic acid sequence showing a 3' PCR site.
  SEQ ID NOS: 22 and 23 are the nucleic acid and amino acid sequence, respectively, of the sequences shown in FIG.12.
  SEQ ID NOS: 24 and 25 are the nucleic acid and amino acid sequence, respectively, of the sequence shown in FIG.13.
  SEQ ID NO: 26 is an amino acid sequence of a Tn5-DICE transposon shown in FIG. 2.
  SEQ ID NO: 27 is an amino acid sequence of a Tn5-HER/neu/SOB transposon shown in FIG. 5.
  SEQ ID NO: 28 is an amino acid sequence of a Tn5-HIV1/SOB transposon shown in FIG. 6.
  SEQ ID NO: 29 is an amino acid sequence of the DICE I transposome shown in

UNITED STATES PATENT AND TRADEMARK OFFICE
CERTIFICATE OF CORRECTION

PATENT NO. : 6,846,622 B1
APPLICATION NO. : 09/979338
DATED : January 25, 2005
INVENTOR(S) : Heffron et al.

It is certified that error appears in the above-identified patent and that said Letters Patent is hereby corrected as shown below:

Column 4, line 52, the following 12 paragraphs should be added: (cont'd)
FIG. 7.
    SEQ ID NO: 30 ia an amino acid sequence of the DICE II transpsome shown in FIG. 8.
    SEQ ID NO: 31 is an amino acid sequence of a *Salmonella*-HER2/neu epitope carrier vaccine shown in FIG. 9.
    SEQ ID NO: 32 is an amino acid sequence of a *Salmonella*-HIV epitope carrier vaccine shown in FIG. 10.
    SEQ ID NO: 33 is a primer sequence.--

Column 5, line 42, "H-2 $K^b$" should be --H-2$K^b$--, and "I-accessible" should be --II-accessible--.

Column 6, line 1, "transposon" should be --a transposon--.

Column 7, lines 18-19, "ATAACTTCGTATAATGTATGCTA TACGAAGTTAT" should be --ATAACTTCGTATAATGTATGCTA TACGAAGTTAT (SEQ ID NO: 14)--.

Column 7, line 25, "MI0494.1" should be --M10494.1--.

Column 7, line 45, "(SEQ ID NO 8)" should be --(SEQ ID NO 20)--.

Column 7, line 49, "of 3'" should be --or 3'--.

Column 7, line 51, "insertion a of" should be --insertion of--.

Column 7, line 56, "0 by" should be --0 bp--.

Column 9, line 60, "a Flt sites" should be --a Frt site--.

Column 10, line 7, "example a recombinase" should be --example of a recombinase--.

Column 10, line 30, "s-called" should be --so-called--.

Column 10, line 54, "express" should be --expresses--.

Column 10, line 59, "maker" should be --marker--.

Column 10, line 62, "In further" should be --In a further--.

UNITED STATES PATENT AND TRADEMARK OFFICE
CERTIFICATE OF CORRECTION

PATENT NO.       : 6,846,622 B1
APPLICATION NO.  : 09/979338
DATED            : January 25, 2005
INVENTOR(S)      : Heffron et al.

It is certified that error appears in the above-identified patent and that said Letters Patent is hereby corrected as shown below:

Column 10, line 65, "resistance" should be --resistant--.

Column 11, lines 24-25, "Adv. Appt. Math" should be --Adv. Appl. Math.--.

Column 11, line 25, "J. Mot. Biol." should be --J. Mol. Biol.--.

Column 11, line 26, "Proc. Natl. Acad Sci." should be --Proc. Natl. Acad. Sci.--.

Column 11, line 42, "60% A," should be --60%,--.

Column 11, line 61, "98%/," should be --98%,--.

Column 12, line 16, "firs:" should be --first--.

Column 12, lines 66-67, a period "." should be added after "U15573)", thus --U15573).--, and a new paragraph should begin with --Transposome:--.

Column 13, lines 49-50, "Arg or Gin for Lys" should be --Arg or Gln for Lys;--.

Column 14, line 31, "such as pair"should be --such as a pair--.

Column 14, line 60, "but is not limited to ampicillin tetracycline" should be --but are not limited to ampicillin, tetracycline--.

Column 15, line 7, "1-$A^b$" should be --I-$A^b$--.

Column 15, line 34, "H-2$K^b$ restricted" should be --H-2$K^b$-restricted--.

Column 15, line 40, "and the carried the ovalbumin" should be --and the carried ovalbumin--.

Column 15, line 51, "The kanarnycin" should be --The kanamycin--.

Column 15, line 58, "(tra-/mob)" should be --(tra-/mob-)--.

Column 15, line 64, "pDES10(F'::Tn5-DICE)" should be -- pDE510(F'::Tn5-DICE)--.

Column 16, line 32, "F'"::Tn5-DICE" should be --F'::Tn5-DICE--.

Column 16, line 41. "83:73540" should be --83:735-40--.

UNITED STATES PATENT AND TRADEMARK OFFICE
CERTIFICATE OF CORRECTION

PATENT NO. : 6,846,622 B1
APPLICATION NO. : 09/979338
DATED : January 25, 2005
INVENTOR(S) : Heffron et al.

It is certified that error appears in the above-identified patent and that said Letters Patent is hereby corrected as shown below:

Column 16, line 66, "120.000" should be --120,000--.

Column 17, line 16, "$1\times10^7$" should be --$1\times10^6$--.

Column 17, line 53, "anti-H-2 $D^b$" should be --anti-H-2$D^b$--.

Column 17, line 53, "The H-2 $K^b$/SIINFEKL" should be --The H-2$K^b$/SIINFEKL--.

Column 17, line 59, "Ga)." should be --Ga.--.

Column 17, line 60, "Anti-H-2 $K^b$/SIINFEKL" should be --Anti-H-2$K^b$/SIINFEKL--.

Column 17, line 63, "ID NO 6);" should be --ID NO 6;--.

Column 17, line 64, "H-2 $K^b$"should be --H-2$K^b$--.

Column 18, line 10, "PE-anti-H-2 $K^b$/SIINFEKL" should be --PE-anti-H-2$K^b$/SIINFEKL--.

Column 18, line 11, "anti-H-2 $D^b$" should be --anti-H-2$D^b$--.

Column 18, line 20, "H-2 Kb/SIINFEKL" should be --H-2$K^b$/SIINFEKL--.

Column 18, line 42, "(amp′ tra$^+$ mob*)" should be --(amp$^r$ tra$^+$ mob$^-$)--.

Column 18, line 44, "1993)an" should be --(1993)) an--.

Column 18, line 48 (specification page 21, line 7), "(amp′ nal′)" should be --(amp$^r$ nal$^r$ )--.

Column 19, line 66, "H-2 $K^b$" should be --H-2$K^b$--.

Column 20, lines 3-4, "H-2 $K^b$/SIINFEKL" should be --H-2$K^b$/SIINFEKL--.

Column 20, line 19, ""H-2 $K^b$/SIINFEKL" should be --H-2$K^b$/SIINFEKL--.

Column 20, line 23, "H-2 $K^b$/SIINFEKL" should be --H-2$K^b$/SIINFEKL--.

Column 20, line 38, "5 mM $K_4Fe(CN)$" should be --5 mM $K_4(CN)_6$--.

UNITED STATES PATENT AND TRADEMARK OFFICE
CERTIFICATE OF CORRECTION

PATENT NO. : 6,846,622 B1
APPLICATION NO. : 09/979338
DATED : January 25, 2005
INVENTOR(S) : Heffron et al.

It is certified that error appears in the above-identified patent and that said Letters Patent is hereby corrected as shown below:

Column 20, line 25, "H-2 $K^b$/SIINFEKL" should be --H-2$K^b$/SIINFEKL--.

Column 20, lines 37-38, "5 mM $K^3Fe(CN)_6$" should be --5 mM $K_3Fe(CN)_6$--.

Column 20, lines 38, "5 mM K4Fe(CN)" should be --5 mM K4(CN)6--.

Column 21, lines 7-8, "SIINFEKL/H-2 $K^b$" should be --SIINFEKL/H-2$K^b$--.

Column 21, line 11, "H-2 $K^b$-restricted"should be --H-2$K^b$-restricted--.

Column 21, line 49, "H-2 $K^b$/SIINFEKL" should be --H-2$K^b$/SIINFEKL--.

Column 23, line 10, "HTLVItax/A2.1." should be --HTLV1tax/A2.1.--.

Column 23, line 11, "H-2$K_b$/HLA-A2*" should be --H-2$K^b$/HLA-A2$^+$--.

Column 23, line 18, "anti-H-2 $D^b$" should be --anti-H-2$D^b$--.

Column 23, line 20, "HTLV-Itax" should be --HTLV-1tax--.

Column 23, line 23, "186(8): 1333-45)to" should be --186(8):1333-45) to--.

Column 23, line 24, "the ta peptide" should be --the tax peptide--.

Column 23, line 29, "A6-TCR Bacteria" should be --A6-TCR. Bacteria--.

Column 23, line 43, "Briefly, This" should be --Briefly, this--.

Column 23, line 55, "CTACTAGTATGGATGGTGTC" should be --CTACTAGTATGGATGGTGTC (SEQ ID NO: 33)--.

Column 23, lines 55-56, "CTAGAACCAGAT GTGTATAAG" should be --CTAGAACCAGAT GTGTATAAG (SEQ ID NO: 21)--.

Column 23, line 63, "Characterization or" should be --Characterization of--.

Column 25, line 4, "with CTS," should be --with $Cr^{51}$--.

UNITED STATES PATENT AND TRADEMARK OFFICE
CERTIFICATE OF CORRECTION

PATENT NO. : 6,846,622 B1
APPLICATION NO. : 09/979338
DATED : January 25, 2005
INVENTOR(S) : Heffron et al.

It is certified that error appears in the above-identified patent and that said Letters Patent is hereby corrected as shown below:

Column 24, line 61, "HER/neu-specific" should be --HER/neu-specific--.

Column 24, line 66, "HLA-A2'" should be --HLA-A2$^+$--.

Column 25, line 22, "my mimicking" should be --by mimicking--.

Column 25, lines 33-34, "(human immunodeficiency virus 1/string of beads)" should be --(human immunodeficiency virus 1/string of beads)--.

Column 25, line 35, "tar epitope" should be --tax epitope--.

Column 25, line 40, "a Nal'" should be --a Nal$^r$--.

Column 25, line 45, "(Ty21 a vaccine strain)" should be (Ty2la vaccine strain)--.

Column 25, line 65, "class 11" should be --class II--.

Column 26, line 12, "have also have" should be --have also had--.

Column 26, line 13, "remove" should be --removed--.

Column 26, line 20, "SIINFEKL" should be --SIINFEKL (SEQ ID NO: 6)--.

Column 26, line 26, "(SEQ ID NO: 8)" should be --(SEQ ID NO: 20)--.

Column 26, line 28, "anti-I-A/$^k$/Hen Egg Lysozyme" should be --anti-I-A$^k$/Hen Egg Lysozyme--.

Column 27, line 7, "In -frame" should be --In-frame--.

Column 27, line 30, "can be use" should be --can be used--.

Column 27, line 44, "limited those" should be --limited to those--.

Column 27, line 50, "and transient" should be --and transient.--.

Column 28, line 27, "#1-2904" should be --#I-2904--.

UNITED STATES PATENT AND TRADEMARK OFFICE
CERTIFICATE OF CORRECTION

PATENT NO. : 6,846,622 B1
APPLICATION NO. : 09/979338
DATED : January 25, 2005
INVENTOR(S) : Heffron et al.

It is certified that error appears in the above-identified patent and that said Letters Patent is hereby corrected as shown below:

Column 29, line 34, "7;2013" should be --7:2013--.

Column 29, lines 35-36, "Proc. Nail. Acad Sci USA" should be --Proc. Natl. Acad. Sci. USA--.

Column 29, line 39, "Proc. Nail. Acad Sci USA" should be --Proc. Natl. Acad. Sci.

Column 30, lines 63-64, "(% formamide)*(600/1)" should be --(% formamide)-(600/1)--

Column 31, line 15, "I=150 base pairs" should be --1=150 base pairs--.

Column 31, line 20, "59.464.4°C" should be --59.4-64.4°C--.

Column 33, line 25, "suppository ran implant" should be --suppository or an implant--.

Column 33, line 51, "90°%" should be --90%--.

Column 34, lines 15-16, "more often ingredients" should be --more of the ingredients--.

Column 34, line 21, "manufacture ," should be --manufacture,--.

Column 34, line 38, "a g ene gun" should be -- a gene gun--.

Column 51, line 13, claim 1, "pathway of eukaryotic cell" should be -- pathway of a eukaryotic cell--.

Column 51, line 28, claim 7, "fit" should be --flt--.

Column 51, line 37, claim 10, "H-2 Kb" should be --H-2Kb--.

Column 52, line 36, claim 27, "(iiii)" should be --(iii)--.

Column 52, line 52, claim 28, "fit" should be --flt--.

Column 52, line 60, claim 31, "H-2 Kb" should be --H-2Kb--.

Column 53, line 2, claim 35, "SEQ ID NO; 3" should be --SEQ ID NO: 3--.

UNITED STATES PATENT AND TRADEMARK OFFICE
CERTIFICATE OF CORRECTION

PATENT NO.         : 6,846,622 B1
APPLICATION NO.    : 09/979338
DATED              : January 25, 2005
INVENTOR(S)        : Heffron et al.

It is certified that error appears in the above-identified patent and that said Letters Patent is hereby corrected as shown below:

Column 54, line 20, claim 45, "H-2 Kb" should be --H-2Kb--.

Column 54, line 31, claim 50, "claim 46" should be --claim 41--.

Signed and Sealed this

Fourteenth Day of November, 2006

JON W. DUDAS
*Director of the United States Patent and Trademark Office*